US012626803B2

(12) United States Patent
Brecin et al.

(10) Patent No.: US 12,626,803 B2
(45) Date of Patent: May 12, 2026

(54) INDIVIDUALIZED ANIMAL MIXED FOOD COMPOSITION

(71) Applicant: MARS, INCORPORATED, McLean, VA (US)

(72) Inventors: Karine Brecin, Aimargues (FR); Sally Perea, Lewisburg, OH (US); Nicolas Ostermann, Aimargues (FR); Jerome Cochet, Aimargues (FR)

(73) Assignee: MARS, INCORPORATED, McLean, VA (US)

( * ) Notice: Subject to any disclaimer, the term of this patent is extended or adjusted under 35 U.S.C. 154(b) by 261 days.

(21) Appl. No.: 18/035,622

(22) PCT Filed: Nov. 8, 2021

(86) PCT No.: PCT/US2021/058464
§ 371 (c)(1),
(2) Date: May 5, 2023

(87) PCT Pub. No.: WO2022/099139
PCT Pub. Date: May 12, 2022

(65) Prior Publication Data
US 2024/0013891 A1 Jan. 11, 2024

Related U.S. Application Data

(60) Provisional application No. 63/198,704, filed on Nov. 6, 2020.

(51) Int. Cl.
| | |
|---|---|
| *G16H 20/60* | (2018.01) |
| *A23K 10/30* | (2016.01) |
| *A23K 20/121* | (2016.01) |
| *A23K 20/147* | (2016.01) |
| *A23K 20/158* | (2016.01) |
| *A23K 20/163* | (2016.01) |
| *A23K 20/174* | (2016.01) |
| *A23K 20/20* | (2016.01) |
| *A23K 20/22* | (2016.01) |
| *A23K 20/24* | (2016.01) |
| *A23K 20/26* | (2016.01) |
| *A23K 50/42* | (2016.01) |
| *A23K 50/48* | (2016.01) |
| *A61B 5/11* | (2006.01) |

(52) U.S. Cl.
CPC ............. *G16H 20/60* (2018.01); *A23K 10/30* (2016.05); *A23K 20/121* (2016.05); *A23K 20/147* (2016.05); *A23K 20/158* (2016.05); *A23K 20/163* (2016.05); *A23K 20/174* (2016.05); *A23K 20/22* (2016.05); *A23K 20/24* (2016.05); *A23K 20/26* (2016.05); *A23K 20/30* (2016.05); *A23K 50/42* (2016.05); *A23K 50/48* (2016.05); *A61B 5/1118* (2013.01); *A61B 2503/40* (2013.01)

(58) Field of Classification Search
CPC ........ A23K 50/40; A23K 50/42; A23K 50/45; A23K 50/48; G16H 20/60
USPC ........................................................ 426/2, 54
See application file for complete search history.

(56) References Cited

U.S. PATENT DOCUMENTS

| | | | | |
|---|---|---|---|---|
| 6,358,546 | B1 * | 3/2002 | Bebiak | A23K 50/40 |
| | | | | 426/805 |
| 6,493,641 | B1 * | 12/2002 | Singh | A23K 50/00 |
| | | | | 426/805 |
| 6,669,975 | B1 * | 12/2003 | Abene | A23K 50/48 |
| | | | | 426/805 |
| 6,733,771 | B1 | 5/2004 | Minard et al. | |
| 12,167,738 | B2 * | 12/2024 | Roche | A23K 20/30 |
| 2003/0004655 | A1 * | 1/2003 | Singh | A23K 50/40 |
| | | | | 702/32 |
| 2003/0009370 | A1 | 1/2003 | Singh et al. | |
| 2004/0091590 | A1 | 5/2004 | Abene et al. | |
| 2004/0253342 | A1 | 12/2004 | Townsend | |
| 2005/0181097 | A1 | 8/2005 | Townsend | |
| 2007/0020355 | A1 | 1/2007 | Schlebusch et al. | |
| 2007/0118295 | A1 * | 5/2007 | Al-Murrani | G16B 20/00 |
| | | | | 702/19 |
| 2008/0154568 | A1 * | 6/2008 | Burghardi | G16H 20/60 |
| | | | | 703/11 |

(Continued)

FOREIGN PATENT DOCUMENTS

| | | | | |
|---|---|---|---|---|
| CA | 2634452 | A1 * | 7/2007 | ......... G06Q 30/0239 |
| CA | 2673552 | A1 * | 7/2008 | ............. A23K 50/40 |

(Continued)

OTHER PUBLICATIONS

U.S. Appl. No. 17/628,823 (US 2022/0256891), filed Jan. 20, 2022 (Aug. 18, 2022).
U.S. Appl. No. 17/628,823, Sep. 12, 2024 Notice of Allowance.
U.S. Appl. No. 17/628,823, Sep. 6, 2024 Request for Continued Examination (RCE).

(Continued)

*Primary Examiner* — Jennifer McNeil
(74) *Attorney, Agent, or Firm* — Baker Botts L.L.P.

(57) ABSTRACT

The present disclosure provides a method for providing an individualized nutritionally complete mixed diet for an animal. In certain embodiments, the animal has one or more pathological condition(s). The present disclosure also provides a device for providing an individualized nutritionally complete mixed diet for an animal. A computer program capable of controlling the device to execute the steps of the method, and a computer-readable medium having stored thereon is further provided herein. The present disclosure additionally provides kits for providing individualized nutritionally complete mixed diet for the animal.

17 Claims, No Drawings

(56) References Cited

U.S. PATENT DOCUMENTS

| | | | | |
|---|---|---|---|---|
| 2009/0175980 A1* | 7/2009 | Willcocks | | A23K 50/40 426/2 |
| 2009/0311366 A1 | 12/2009 | Biourge et al. | | |
| 2013/0059028 A1* | 3/2013 | Foy | | A23K 50/40 426/74 |
| 2013/0226729 A1 | 8/2013 | Reed et al. | | |
| 2014/0141134 A1* | 5/2014 | Johnson | | A23K 40/00 426/231 |
| 2014/0272028 A1* | 9/2014 | Donavon | | G06Q 50/04 707/769 |
| 2015/0072048 A1* | 3/2015 | Potthoff | | G06Q 30/0621 705/26.5 |
| 2015/0164112 A1* | 6/2015 | Delaney | | A23L 33/175 426/2 |
| 2016/0135484 A1 | 5/2016 | Ecochard | | |

FOREIGN PATENT DOCUMENTS

| | | | | |
|---|---|---|---|---|
| CA | 2 450 055 C | 8/2010 | | |
| CN | 1543316 A | 11/2004 | | |
| CN | 103327829 A | 9/2013 | | |
| CN | 105209903 A | 12/2015 | | |
| CN | 105263318 A | 1/2016 | | |
| EP | 1 093 719 A2 | 4/2001 | | |
| JP | 2004-529656 A | 9/2004 | | |
| JP | 2009-544297 A | 12/2009 | | |
| JP | 2016-518818 A | 6/2016 | | |
| KR | 101 671 888 B1 | 11/2016 | | |
| WO | 8202650 A1 | 8/1982 | | |
| WO | WO-0041575 A1 * | 7/2000 | | A01K 5/02 |
| WO | WO 01/69487 A1 | 9/2001 | | |
| WO | WO-02102271 A2 * | 12/2002 | | A23K 50/40 |
| WO | WO 2014/078856 A1 | 5/2014 | | |
| WO | WO-2017174383 A1 * | 10/2017 | | G16H 20/60 |
| WO | WO-2019110542 A1 * | 6/2019 | | G16H 20/60 |
| WO | WO-2021061743 A1 * | 4/2021 | | A23K 20/147 |
| WO | 2022099139 A1 | 5/2022 | | |

OTHER PUBLICATIONS

U.S. Appl. No. 17/628,823, Aug. 19, 2024 Notice of Allowance.
U.S. Appl. No. 17/628,823, Aug. 5, 2024 Response after Final Action.
U.S. Appl. No. 17/628,823, Jun. 7, 2024 Final Office Action.
U.S. Appl. No. 17/628,823, May 24, 2024 Response to Non-Final Office Action.
U.S. Appl. No. 17/628,823, Apr. 24, 2024 Non-Final Office Action.
International Search Report mailed Jan. 19, 2021 in International Application No. PCT/US2020/052172.
National Research Council, 1985, Nutritional Requirements for dogs, National Academy Press, Washington DC or Association of America Feed Control Officials, Official Publication 1996.
Tan Shiwen and Huang Guiping, "Research progress of computer application in animal husbandry and veterinary medicine," Guizhou Animal Husbandry and Veterinary Medicine, 25(5):1-10 (2001).
U.S. Appl. No. 17/628,823 (US 2022/0256891), Jan. 20, 2022 (Aug. 18, 2022).
U.S. Appl. No. 17/628,823. Sep. 14, 2024 Notice of Allowance.
International Search Report mailed Mar. 9, 2022 in International Application No. PCT/US2021/058464.
Regulation (EC) No. 767/2009 of the European Parliament and of the Council of Jul. 13, 2009, 45 pages.

* cited by examiner

INDIVIDUALIZED ANIMAL MIXED FOOD COMPOSITION

CROSS-REFERENCE TO RELATED APPLICATIONS

This application is a U.S. National Stage Patent Application under 35 U.S.C. § 371 of International Patent Application No. PCT/US2021/058464, filed on Nov. 8, 2021, which claims priority to U.S. Provisional Application Ser. No. 63/198,704, filed on Nov. 6, 2020, the contents of each of which are incorporated herein by reference in their entireties, and to which priority is claimed.

FIELD OF THE DISCLOSURE

The present disclosure relates to the field of functional food for animals, and especially for companion animals such as, e.g., cats and dogs.

BACKGROUND OF THE DISCLOSURE

There is an increasing awareness of the importance of a proper diet for the health maintenance and disease prevention or treatment of animals, especially companion animals. Customized diets for various life stages and conditions are currently available for such animals. However, although a high number of suppliers and products are available to pet care product consumers, it can take significant time, effort, and investigation for a customer to determine which product (s) best suits a particular animal's need among the large number of alternatives. While veterinarians and other professionals can assist in recommending a given brand of pet food for a particular pet, pet foods are typically mass manufactured to meet the needs of an average pet, with the pet's age and/or size being primary factors that are taken into consideration for the development of such pet foods.

Thus, there is a need for individualized food products for animals, and more particularly, for individualized mixed feedings, which are particularly convenient for storage and feeding, and which are less prone to spoilage.

Nutritional needs, however, vary from pet to pet, and a customized regimen of appropriate nutrients for a particular pet or breed of pet would be beneficial. But in light of the practical difficulties and expenses of tailoring a custom diet for a particular pet, consumers are often forced to choose from a limited variety of available mass-produced pet foods and products. With the view of fulfilling the pet owners' need for adapted food compositions, several manufacturers have conceived systems allowing delivering foodstuff that better correlates with the specific nutritional requirements of their companion animal.

Illustratively, Purina's Company website provides potential customers the opportunity for the delivery of customized dog food after having registered specific description parameters of their pet, such as breed, sex, age, weight, level of physical activity, eating habits, coat's features, skin's features, stool consistency, kind of meal preferences (notably protein preference).

U.S. Pat. No. 6,358,546 is directed toward methods for customizing pet food, wherein a user input is used to form an individual pet profile, which is used to generate a customized pet food formula.

WO 01/69487 discloses the principle methods and apparatus for customizing pet food that utilize an integrated internet-based customer interface and workflow process management. Completely custom-made food category provides a practically unlimited choice of customized pet food formulation in which pet food is manufactured from raw ingredients in a respective individual pet profile. A more limited range of customized formulations can be manufactured from pre-mixed components selected by a purchaser in a respective individual pet profile.

U.S. Pat. No. 6,669,975 is directed to a customized dietary health management system for pets. This management system includes manufacturing a dry kibble product by blending pre-made dry kibbles, adding additional functional ingredients, and then packaging. A customized food product is obtained by selecting at least one formulation of pre-made dry kibble, separating a predetermined volume of the at least one formulation of the pre-made dry kibble, blending the predetermined volume of pre-made dry kibble, coating the volume of dry kibble with a selected mixture of functional ingredients and then packaging the resulting product.

U.S. Pat. No. 6,493,641 pertains to methods for manufacturing pet foods customized to the health and nutrition requirements of an individual pet. Those methods include obtaining an individual pet profile for the pet, obtaining an analysis from a biological sample of the pet, processing the individual pet profile and the biological sample analysis to create a first pet food formula specific to the user input individual pet profile and the biological sample analysis, and manufacturing the pet food according to the first pet food formula. In some embodiments, the method includes suggesting a pre-manufactured kibble that correlates with the processed pet profile, suggesting a pre-manufactured additive that correlates with the processed pet profile, and providing a set of feeding instructions for the pet.

U.S. Publication No. 2007/0118295 discloses a concept of methods and systems for designing animal food compositions in which an important component is the processing of information relating to the functional genomic profile of animals.

U.S. Publication No. 2014/0272028 which relates to systems and methods for collecting specific pet information and utilizing that information to create a custom pet food product. According the disclosed methods, based upon a correlation by a computer, the computer suggests a pre-manufactured kibble or blend from a number of possible pre-manufactured kibbles or blends and creates a pet food additive based on the pet food product formulation specific to the pet and in accordance with the pet profile of the pet.

U.S. Pat. No. 6,733,771 and EP1093719 both relate to methods and apparatus for the administration of food to horses, said methods being defined by a specific packaging.

U.S. Publication No. 2015/0072048, although relating to a computer-implemented method of providing a personalized diet, does not teach nor mention the use of pre-made compositions, and more particularly of pre-made composition which are not nutritionally complete.

WO 2014/078856 discloses systems and methods for creating a customized blend of pet food. Those methods include a step of creating a first environment profile for the pet consisting of inputting pet characteristics in a computer system, such as age, breed, weight and food preferences. The method also includes acquiring data, which data can include published pet nutrition information, comparing the data to the first environmental profile, and then generating the nutritional target from the said data and the first environmental profile, and then a nutritional blend recipe is generated on a blend customization computer system. Once a nutritional blend recipe has been generated, a nutritional blend is prepared on the basis of a plurality of pre-blend formulae contained in a pre-blend database contained in a database server, through a customized blending system. Pre-blends can be configured from any suitable ingredients of kibble products and can be created at a blending center. The customized blend recipe can call for a first percentage of a first pre-blend, a second percentage of a second pre-blend and a third percentage of a third pre-blend to create a customized blend of kibble that can match a nutrition target for the pet.

Still, the preparation of food compositions which are suitable for animal consumption remains difficult in particular if mixed feeding compositions are desired. Hence, there remains a need for improved systems and methods for manufacturing individualized pet food compositions, e.g., dry or wet pet food compositions. In particular, there remains a need for such systems and methods, which would remain cost-effective. There also remains a need for such systems and methods, for preparing mixed compositions suitable for animals with pathological condition(s).

More particularly, the preparation of a suitable individualized mixed compositions suitable for animals with pathological condition(s) has not been addressed by any existing method. It is known that many pet owners are willing and would prefer to feed their animal(s) with both wet and dry food compositions. However, managing to have a balanced diet program with both wet and dry compositions is often difficult even when the animal is healthy. Providing a balanced diet of wet and dry food is more difficult in the case of an individualized nutrition aiming at treating and/or preventing pathological condition(s). The present disclosure aims to provide a solution to these issues.

SUMMARY OF THE DISCLOSURE

The purpose and advantages of the disclosed subject matter will be set forth in and are apparent from the description that follows, as well as will be learned by practice of the disclosed subject matter. Additional advantages of the disclosed subject matter will be realized and attained by the compositions and devices particularly pointed out in the written description and claims hereof.

To achieve these and other advantages and in accordance with the purpose of the disclosed subject matter, as embodied and broadly described, the disclosed subject matter includes a method for providing an individualized nutritionally complete mixed diet for an animal, with said diet having a wet portion containing one pre-made wet composition combined with a dry portion containing at least two pre-made dry compositions, the method including the steps of:

a) providing an individual physiological profile of an animal, and optionally an individual pathological profile of the animal, from one or more values indicative of a physiological status, and optionally a medical status, of the said animal, whereby an individual general profile is generated;

b) processing the individual general profile to determine a nutrient requirement (NR), a maintenance energy requirement (MER) and a wet-dry ratio (WDR) specific to the animal;

c) selecting, based on the NR, one pre-made wet composition from a plurality of distinct pre-made wet compositions, and at least two distinct pre-made dry compositions from a plurality of distinct pre-made dry compositions;

d) determining, based on the MER and the WDR, a fixed amount of the pre-made wet composition to obtain the wet portion of the nutritionally complete mixed diet;

e) determining, based on the MER, the WDR and the fixed amount of the pre-made wet composition, an adjusted amount of each of the at least two distinct pre-made dry compositions to obtain the dry portion of the nutritionally complete mixed diet;

f) combining the wet portion and the dry portion to obtain a nutritionally complete mixed diet;

wherein none of the selected distinct pre-made dry compositions consists of a nutritionally complete diet on their own.

In certain embodiments, the selection of the pre-made wet composition and the at least two pre-made dry compositions in step c) are realized simultaneously or sequentially.

In certain embodiments, the method further includes a step of providing an individual pathological profile of the animal from one or more values indicative of a medical status of the animal.

In certain embodiments, the WDR ratio is between 15:85 to 40:60.

In certain embodiments, the dry portion includes at least 5 distinct pre-made dry compositions selected from a plurality of distinct pre-made dry compositions.

In certain embodiments, the pre-made dry compositions have a moisture level ranging from about 1% to about 14% w/w.

In certain embodiments, the said pre-made dry compositions include dry kibbles.

In certain embodiments, the wet portion includes a pre-made wet composition having a moisture level greater than about 60% w/w.

In certain embodiments, the one or more values indicative of a physiological status of the said animal are selected from the group consisting of animal's breed, animal's age, animal's actual weight, animal's targeted weight, animal's Body Condition Score (BCS), animal's activity, animal's lifestyle, animal's sexual status, and animal's gestation status.

In certain embodiments, the animal is a cat and the one or more values indicative of a medical status of the said animal are selected from the group consisting of Post weight loss, Overweight, Obesity, Osteoarthritis, Mobility risk factors, Chronic Kidney Disease (CKD) Stage I, II, III or IV, Proteinuria, Struvite urolith dissolution, Struvite urolith prevention, Calcium Oxalate urolith (CaOx) prevention, Calcium Phosphate urolith (CaP) prevention, Idiopathic cystitis, Poor skin and coat, Atopy, non-food related dermatopathies, Dental Calculus, Acute or chronic diarrhea, Acute or chronic vomiting, Gastritis, Enteritis, Colitis, Maldigestion, Malabsorption, Diabetes mellitus, Pancreatitis, Exocrine pancreatic insufficiency (EPI), and Hyperlipidemia.

In certain embodiments, the animal is a dog and the one or more values indicative of a medical status of the said animal are selected from the group consisting of Post weight loss, Overweight, Obesity, Osteoarthritis, Mobility risk factors, CKD Stage I, II, III or IV, Proteinuria, Struvite urolith dissolution, Struvite urolith prevention, Calcium Oxalate urolith (CaOx) prevention, Calcium Phosphate urolith (CaP) prevention, Idiopathic cystitis, Poor skin and coat, Atopy, non-food related dermatopathies, Dental Calculus, Acute or chronic diarrhea, Acute or chronic vomiting, Gastritis, Enteritis, Colitis, Maldigestion, Malabsorption, Diabetes mellitus, Pancreatitis, Exocrine pancreatic insufficiency (EPI), Hyperlipidemia, and Adverse food reaction.

In certain embodiments, the animal has one or more pathological conditions.

In certain embodiments, the method includes a computer-implemented method.

In certain embodiments, the nutritionally complete diet further includes at least one additional ingredient selected from the group consisting of a source of proteins, a source of vitamins, a source of fats and a source of minerals.

In other aspects, the present disclosure relates to means and devices for providing or implementing an individualized nutritionally complete mixed diet for an animal, having means adapted to execute the steps of the method described above. Hence, in some aspects, the present disclosure also relates to a computer program including instructions to cause the device described above to execute the steps of the method. The present disclosure also relates to a computer-readable medium having stored thereon the computer program described above.

In certain embodiments, the present disclosure provides a device for providing an individualized nutritionally complete mixed diet for an animal including a wet portion including one pre-made wet composition combined with a dry portion including at least two distinct pre-made dry compositions, said device having means adapted to execute the steps of:

a) providing an individual physiological profile of an animal from one or more values indicative of a physiological status of the animal, whereby an individual general profile is generated;

b) processing the individual general profile to determine a nutrient requirement (NR), a maintenance energy requirement (MER) and a wet-dry ratio (WDR) specific to the animal;

c) selecting, based on the NR of the step b), one pre-made wet composition from a plurality of distinct pre-made wet compositions, and at least two distinct pre-made dry compositions from a plurality of distinct pre-made dry compositions;

d) determining, based on the MER and the WDR, a fixed amount of the pre-made wet composition to obtain the wet portion of the nutritionally complete mixed diet;

e) determining, based on the MER and the WDR, the adjusted amount of each of the at least two pre-made dry compositions and mixing them together to obtain the dry portion of the nutritionally complete mixed diet;

f) combining the wet portion and the dry portion to obtain a nutritionally complete mixed diet;

wherein none of the said selected distinct pre-made dry compositions includes a nutritionally complete diet alone.

In certain embodiments, the device has a further mean adapted to execute the step of providing an individual pathological profile of an animal from one or more values indicative of a medical status of the said animal.

In certain embodiments, the present disclosure provides a computer program including instructions to cause the device as disclosed herein to execute the steps of the method.

In certain embodiments, the present disclosure provides a computer-readable medium having stored thereon the computer program as provides herein.

In still yet other aspects, the present disclosure also provides a kit for preparing a nutritionally complete mixed diet, including at least two or more dry compositions from a list combined with at least one wet composition from a list. In certain embodiments, the disclosure provides a kit for preparing a nutritionally complete mixed diet including a wet portion containing one pre-made wet composition combined with a dry portion containing at least two distinct pre-made dry compositions, said at least two or more distinct pre-made dry compositions being selected from:

dry composition A with at least about 1.5% of sodium, at least about 38% of protein and no more than about 10% of fat, relative to the total weight of the composition on a dry-matter basis;

dry composition B with at least about 0.5% of psyllium tegument, at least about 35% of protein, at least about 0.5% of calcium and no more than about 0.7% of phosphorus, relative to the total weight of the composition on a dry-matter basis;

dry composition C with at least about 37% of protein, at least about 1.5% of sodium, at least about 2.5% of chloride and at least about 0.6% of EPA and/or DHA, relative to the total weight of the composition on a dry-matter basis;

dry composition D with at least about 20% of TDF, at least about 38% of protein, no more than about 9% of fat and at least about 1.3% of potassium, relative to the total weight of the composition on a dry-matter basis;

dry composition E with at least about 3.5% of linoleic acid, at least about 0.4% of phosphorus and no more than about 7% of TDF, relative to the total weight of the composition on a dry-matter basis;

dry composition F with at least about 0.55% of EPA and/or DHA, relative to the total weight of the composition on a dry-matter basis;

dry composition G with at least about 0.8% of EPA/DHA and at least about 1.5% of sodium, relative to the total weight of the composition on a dry-matter basis;

dry composition H with at least about 20% of fat, no more than about 0.5% of calcium and at least about 5% of linoleic acid, relative to the total weight of the composition on a dry-matter basis;

dry composition I with at least about 4% of psyllium tegument, relative to the total weight of the composition on a dry-matter basis;

dry composition J with no more than about 6 ppm of total copper, relative to the total weight of the composition on a dry-matter basis.

dry composition A' with at least about 1.7% of sodium and no more than about 10% of fat, relative to the total weight of the composition on a dry-matter basis;

dry composition B' with at least about 40% of protein and at least about 1.5% of calcium, relative to the total weight of the composition on a dry-matter basis;

dry composition C' with no more than about 6% of fat and no more than about of calcium, no more than about 0.45% of phosphorus, relative to the total weight of the composition on a dry-matter basis;

dry composition D' with at least about 22% of fat, at least about 0.55% of EPA and/or DHA and at least about 5% of linoleic acid, relative to the total weight of the composition on a dry-matter basis;

dry composition E' with no more than about 7% of fat, at least about 25% of TDF and at least about 35% of protein, relative to the total weight of the composition on a dry-matter basis;

dry composition F' with no more than about 12% of protein, at least about 22% of fat, at least about 0.25% of phosphorus, no more than about 0.5% of calcium and at least about 0.7% of EPA and/or DHA, relative to the total weight of the composition on a dry-matter basis;

dry composition G' with no more than about 0.35% of calcium, no more of about of phosphorus, at least about 1.6% of sodium and at least about 25% of TDF, relative to the total weight of the composition on a dry-matter basis;

dry composition H' with no more than about 6% of fat and at least about 1.6% of sodium, relative to the total weight of the composition on a dry-matter basis;

dry composition I' with no more than about 0.21% of sodium and at least about 1.65% of total arginine, relative to the total weight of the composition on a dry-matter basis;

dry composition J' with no more than about 6 ppm of total copper and no more than about 20% of fat, relative to the total weight of the composition on a dry-matter basis;

dry composition K' with at least about 40% of protein and no more than about 23% of starch, relative to the total weight of the composition on a dry-matter basis;

dry composition L' with at least about 21% of total dietary fiber, relative to the total weight of the composition on a dry-matter basis.

Hence, according to another aspect, the disclosure also provides a kit for preparing a nutritionally complete mixed diet including a wet portion containing one pre-made wet composition combined with a dry portion containing at least two distinct pre-made dry compositions, said one pre-made wet composition being selected from:

wet composition 1 with no more than about 45 g/Mcal crude fat, no more than about 1.5 g/Mcal phosphorus, at least about 1.6 g/Mcal EPA+DHA, and at least about 240 mg/Mcal glucosamine+chondroitin;

wet composition 2 with at least about 1.8 g/Mcal EPA+DHA, at least about 240 mg/Mcal glucosamine+chondroitin, at least about 40 mg/Mcal zinc, at least about 37.5 mg/Mcal vitamin B5, and at least about 125 mg/Mcal vitamin B3 (niacin);

wet composition 3 with at least about 3 g/Mcal sodium, at least about 50 mg/Mcal L-carnitine, at least about 110 g/Mcal protein, no more than about 35 g/Mcal crude fat, at least about 0.26 g/Mcal Lactium® (milk protein hydrolysate), at least about 0.98 g/Mcal tryptophan, and at least about 200% of the minimum NRC recommended amount in mg/Mcal in essential amino acids;

wet composition 4 with at least about 50 mg/Mcal L-carnitine, at least about 110 g/Mcal protein, no more than about 35 g/Mcal crude fat, at least about 50 mg/Mcal zinc, and at least about 200% of the minimum NRC recommended amount in mg/Mcal in essential amino acids;

wet composition 5 with at least about 1.8 g/Mcal of EPA+DHA, at least about 80% of moisture in the finish product, at least about 0.26 g/Mcal Lactium® (milk protein hydrolysate), at least about 0.98 g/MCal tryptophan, and no more than about 1.7 g/Mcal phosphorus;

wet composition 6 with at least about 9.3 g/Mcal linoleic acid (LA), at least about alpha-linoleic acid (ALA), at least about 37.5 mg/Mcal vitamin B5, and at least about 125 mg/Mcal vitamin B3 (niacin);

wet composition 7 with no more than about 67 g/Mcal protein, no more than about 1.0 g/Mcal phosphorus, at least about 1.7 g/Mcal potassium, at least about 1 g/Mcal EPA+DHA, at least about 9.3 g/Mcal linoleic acid (LA), and at least about 0.42 g/Mcal alpha-linoleic acid (ALA);

wet composition 8 with at least about 1.5 g/Mcal EPA+DHA, at least about 200 mg/Mcal glucosamine+chondroitin, no more than about 1.5 g/Mcal phosphorus, at least about 9.3 g/Mcal linoleic acid (LA), and at least about 0.42 g/Mcal alpha-linoleic acid (ALA);

wet composition 9 with at least about 1 g/Mcal EPA+DHA, no more than about 1.7 g/Mcal phosphorus at least about 7.6 g/Mcal linoleic acid (LA), and at least about alpha-linoleic acid (ALA);

wet composition 10 with no more than about 35 g/Mcal crude fat, at least about 6.0 g/Mcal linoleic acid (LA), at least about 1 g/Mcal EPA+DHA, and no more than about 1.7 g/Mcal phosphorus.

For the dry product, the lower and upper amounts of each ingredient, when not explicitly reported, are dependent upon the total dry-matter weight of each composition, and the presence of the other recited compounds. However, each final range is readily determinable by those skilled in the art.

For wet products, the lower and upper amounts of each ingredient are expressed in units per Mcal, and more particularly in g/Mcal.

Knowing the dry matter content of the said finish product and its energetic value allows for the calculation of equivalences:

$$\text{Unit per 100 g dry matter} = [(\text{unit per 1000 kcal}*\text{energy in kcal/kg of finish product})/(\text{dry matter per 100 g of finish product}*100)]$$

$$\text{Or Unit per 1000 kcal} = [(\text{unit per 100 g dry matter}*\text{dry matter per 100 g of finish product}*100)/\text{energy in kcal/kg of finish product}]$$

Within the present disclosure, the energetic value is predicted using NRC 2006 TDF equation.

In certain embodiments, the present disclosure provides a computer-implemented method including receiving, at a server computer from a client computing device, a digital input including one or more values indicative of a physiological status of an animal, the server computer including computer memory digitally storing composition data specifying a plurality of pre-made wet compositions and a plurality of pre-made dry compositions, executing, at the server computer, first programmed instructions to generate and digitally store in the computer memory an individual general profile of the animal by inferring, at least partly based on the one or more values, an individual physiological profile of the animal, executing, at the server computer, second programmed instructions to determine, at least partly based on the individual general profile of the animal, a nutrient requirement (NR), a maintenance energy requirement (MER), and a wet-dry ratio (WDR), executing, at the server computer, third programmed instructions to select, at least partly based on the NR, one of the pre-made wet compositions and at least two of the pre-made dry compositions, the at least two of the pre-made dry compositions being distinct executing, at the server computer, fourth programmed instructions to determine, at least partly based on the MER and the WDR, a fixed amount of the pre-made wet composition to obtain a wet portion of a nutritionally complete mix diet, executing, at the server computer, fifth programmed instructions to determine, at least partly based on the MER, the WDR, and the fixed amount of the pre-made wet composition, an adjusted amount of each of the at least two pre-made dry compositions to obtain a dry portion of the nutritionally complete mixed diet, and displaying, in a graphical user interface on a device display of the client computing device, a representation of the nutritionally complete mixed diet, the representation indicating the wet portion and the dry portion. In certain embodiments, the WDR is between 15:85 to 40:60. In certain embodiments, the dry portion includes at least distinct pre-made dry compositions of the plurality of pre-made dry compositions. In certain embodiments, the pre-made dry compositions each have a moisture level between about 1% and about 14% w/w. In certain embodiments, at least one of the pre-made dry compositions includes dry kibbles. In certain embodiments, wet portion includes a pre-made wet composition having a moisture level greater than about 60% w/w. In certain embodiments, the one or more values indicative of a physiological status of the animal are selected from the group consisting of animal's breed, animal's age, animal's actual weight, animal's targeted weight, animal's Body Condition Score (BCS), animal's activity, animal's lifestyle, animal's sexual status, and animal's gestation status.

In certain embodiments, the computer-implemented method further includes receiving, at the server computer, one or more values indicative of a medical status of the animal, and generating, at the server computer, an individual pathological profile of the animal from the one or more values indicative of the medical status of the animal. In certain embodiments, the animal has one or more pathological conditions. In certain embodiments, the animal is a cat and the one or more values indicative of the medical status of the animal are selected from the group consisting of Post weight loss, Overweight, Obesity, Osteoarthritis, Mobility risk factors, Chronic Kidney Disease (CKD) Stage I, II, III or IV, Proteinuria, Struvite urolith dissolution, Struvite urolith prevention, Calcium Oxalate urolith (CaOx) prevention, Calcium Phosphate urolith (CaP) prevention, Idiopathic cystitis, Poor skin and coat, Atopy, non-food related dermatopathies, Dental Calculus, Acute or chronic diarrhea, Acute or chronic vomiting, Gastritis, Enteritis, Colitis, Maldigestion, Malabsorption, Diabetes mellitus, Pancreatitis, Exocrine pancreatic insufficiency (EPI), and Hyperlipidemia. In certain other embodiments, the animal is a dog and the one or more values indicative of the medical status of the animal are selected from the group consisting of Post weight loss, Overweight, Obesity, Osteoarthritis, Mobility risk factors, CKD Stage I, II, III or IV, Proteinuria, Struvite urolith dissolution, Struvite urolith prevention, Calcium Oxalate urolith (CaOx) prevention, Calcium Phosphate urolith (CaP) prevention, Idiopathic cystitis, Poor skin and coat, Atopy, non-food related dermatopathies, Dental Calculus, Acute or chronic diarrhea, Acute or chronic vomiting, Gastritis, Enteritis, Colitis, Maldigestion, Malabsorption, Diabetes mellitus, Pancreatitis, Exocrine pancreatic insufficiency (EPI), Hyperlipidemia, and Adverse food reaction.

In certain embodiments, the dry portion includes two distinct pre-made dry compositions each selected from the group consisting of:

dry composition A with at least about 1.5% of Sodium, at least about 38% of protein and no more than about 10% of fat, relative to the total weight of the composition on a dry-matter basis;

dry composition B with at least about 0.5% of Psyllium Tegument, at least about 35% of protein, at least about 0.5% of calcium and no more than about 0.7% of Phosphorus, relative to the total weight of the composition on a dry-matter basis;

dry composition C with at least about 37% of protein, at least about 1.5% of Sodium, at least about 2.5% of chloride and at least about 0.6% of EPA and/or DHA, relative to the total weight of the composition on a dry-matter basis;

dry composition D with at least about 20% of TDF, at least about 38% of protein, no more than about 9% of fat and at least about 1.3% of Potassium, relative to the total weight of the composition on a dry-matter basis;

dry composition E with at least about 3.5% of linoleic acid, at least about 0.4% of Phosphorus and no more than about 7% of TDF, relative to the total weight of the composition on a dry-matter basis;

dry composition F with at least about 0.55% of EPA and/or DHA, relative to the total weight of the composition on a dry-matter basis;

dry composition G with at least about 0.8% of EPA/DHA and at least about 1.5% of Sodium, relative to the total weight of the composition on a dry-matter basis;

dry composition H with at least about 20% of fat, no more than about 0.5% of Calcium and at least about 5% of linoleic acid, relative to the total weight of the composition on a dry-matter basis;

dry composition I with at least about 4% of Psyllium Tegument, relative to the total weight of the composition on a dry-matter basis;

dry composition J with no more than about 6 ppm of total copper, relative to the total weight of the composition on a dry-matter basis;

dry composition A' with at least about 1.7% of Sodium and no more than about 10% of fat, relative to the total weight of the composition on a dry-matter basis;

dry composition B' with at least about 40% of protein and at least about 1.5% of calcium, relative to the total weight of the composition on a dry-matter basis;

dry composition C' with no more than about 6% of fat, no more than about of Calcium and no more than about 0.45% of Phosphorus, relative to the total weight of the composition on a dry-matter basis;

dry composition D' with at least about 22% of fat, at least about 0.55% of EPA and/or DHA and at least about 5% of linoleic acid, relative to the total weight of the composition on a dry-matter basis;

dry composition E' with no more than about 7% of fat, at least about 25% of TDF and at least about 35% of protein, relative to the total weight of the composition on a dry-matter basis;

dry composition F' with no more than about 12% of protein, at least about 22% of fat, at least about 0.25% of phosphorus, no more than about 0.5% of calcium and at least about 0.7% of EPA and/or DHA, relative to the total weight of the composition on a dry-matter basis;

dry composition G' with no more than about 0.35% of Calcium, no more than about 0.35% of phosphorus, at least about 1.6% of Sodium and at least about 25% of TDF, relative to the total weight of the composition on a dry-matter basis;

dry composition H' with no more than about 6% of fat and at least about 1.6% of sodium, relative to the total weight of the composition on a dry-matter basis; and wherein none of the said pre-made dry compositions consists of a nutritionally complete composition;

dry composition I' with no more than about 0.21% of Sodium and at least about 1.65% of total arginine, relative to the total weight of the composition on a dry-matter basis;

dry composition J' with no more than 6 ppm of total copper and no more than about 20% of fat, relative to the total weight of the composition on a dry-matter basis;

dry composition K' with at least about 40% of protein and no more than about 23% of starch, relative to the total weight of the composition on a dry-matter basis; and dry composition L' with at least about 21% of total dietary fiber, relative to the total weight of the composition on a dry-matter basis.

In certain embodiments, the wet portion includes one pre-made wet composition selected from the group consisting of:

wet composition 1 with no more than about 45 g/Mcal Crude fat, no more than about 1.5 g/Mcal Phosphorus, at least about 1.6 g/Mcal EPA+DHA, and at least about 240 mg/Mcal Glucosamine+chondroitin;

wet composition 2 with at least about 1.8 g/Mcal EPA+DHA, at least about 240 mg/Mcal Glucosamine+chondroitin, at least about 40 mg/Mcal Zinc, at least about 37.5 mg/Mcal Vitamin B5, and at least about 125 mg/Mcal Vitamin B3 (niacin);

wet composition 3 with at least 3 g/Mcal Sodium, at least about 50 mg/Mcal L-Carnitine, at least about 110 g/Mcal Protein, no more than about 35 g/Mcal Crude Fat, at least about 0.26 g/Mcal Lactium® (milk protein hydrolysate), at least about 0.98 g/Mcal Tryptophan, and at least about 200% of the minimum NRC recommended amount in mg/Mcal in essential amino acids;

wet composition 4 with at least about 50 mg/Mcal L-carnitine, at least about 110 g/Mcal Protein, no more than about 35 g/Mcal Crude Fat, at least about 50 mg/Mcal Zinc, and at least about 200% of the minimum NRC recommended amount in mg/Mcal in essential amino acids;

wet composition 5 with at least about 1.8 g/Mcal of EPA+DHA, at least about 80% of moisture in the finish product, at least about 0.26 g/Mcal Lactium® (milk protein hydrolysate), at least about 0.98 g/MCal tryptophan, and no more than about 1.7 g/Mcal Phosphorus;

wet composition 6 with at least about 9.3 g/Mcal Linoleic acid (LA), at least about 0.42 g/Mcal Alpha-linoleic acid (ALA), at least about 37.5 mg/Mcal Vitamin B5, and at least about 125 mg/Mcal Vitamin B3 (niacin);

wet composition 7 with no more than about 67 g/Mcal Protein, no more than about 1 g/Mcal Phosphorus, at least about 1.7 g/Mcal Potassium, at least 1 g/Mcal EPA+DHA, at least about 9.3 g/Mcal Linoleic acid (LA), and at least about 0.42 g/Mcal Alpha-linoleic acid (ALA);

wet composition 8 with at least about 1.5 g/Mcal EPA+DHA, at least about 200 mg/Mcal Glucosamine+Chondroitin, no more than about 1.5 g/Mcal Phosphorus, at least about 9.3 g/Mcal Linoleic acid (LA), and at least about 0.42 g/Mcal Alpha-linoleic acid (ALA);

wet composition 9 with at least about 1 g/Mcal EPA+DHA, no more than about 1.7 g/Mcal phosphorus at least about 7.6 g/Mcal Linoleic acid (LA), and at least about Alpha-linoleic acid (ALA); and wet composition 10 with no more than about 35 g/Mcal Crude Fat, at least about 6 g/Mcal Linoleic acid (LA), at least about 1 g/Mcal EPA+DHA, and no more than about 1.7 g/Mcal Phosphorus.

In certain embodiments, the present disclosure provides a computer-implemented method including:

digitally storing composition data specifying a plurality of pre-made wet compositions and a plurality of pre-made dry compositions;

receiving one or more values indicative of a physiological status of an animal;

programmatically generating and digitally storing an individual general profile of the animal by inferring, at least partly based on the one or more values, an individual physiological profile of the animal;

programmatically determining, at least partly based on the individual general profile of the animal, a nutrient requirement (NR), a maintenance energy requirement (MER), and a wet-dry ratio (WDR);

programmatically selecting, at least partly based on the NR, one of the pre-made wet compositions and at least two of the pre-made dry compositions, the at least two of the pre-made dry compositions being distinct;

programmatically determining, at least partly based on the MER and the WDR, a fixed amount of the pre-made wet composition to obtain a wet portion of a nutritionally complete mix diet;

programmatically determining, at least partly based on the MER, the WDR, and the fixed amount of the pre-made wet composition, an adjusted amount of each of the at least two pre-made dry compositions to obtain a dry portion of the nutritionally complete mixed diet; and causing displaying, in a graphical user interface, a representation of the nutritionally complete mixed diet, the representation indicating the wet portion and the dry portion. In certain embodiments, the WDR is between 15:85 to 40:60. In certain embodiments, the dry portion includes at least 5 distinct pre-made dry compositions of the plurality of pre-made dry compositions. In certain embodiments, the pre-made dry compositions each have a moisture level between about 1% and about 14% w/w. In certain embodiments, at least one of the pre-made dry compositions includes dry kibbles. In certain embodiments, the wet portion includes a pre-made wet composition having a moisture level greater than about 60% w/w. In certain embodiments, the one or more values indicative of a physiological status of the animal are selected from the group consisting of animal's breed, animal's age, animal's actual weight, animal's targeted weight, animal's Body Condition Score (BCS), animal's activity, animal's lifestyle, animal's sexual status, and animal's gestation status.

In certain embodiments, the computer-implemented method of the present disclosure further includes receiving one or more values indicative of a medical status of the animal, and programmatically generating an individual pathological profile of the animal from the one or more values indicative of the medical status of the animal. In certain embodiments, the animal has one or more pathological conditions. In certain embodiments, the animal is a cat and the one or more values indicative of the medical status of the animal are selected from the group consisting of Post weight loss, Overweight, Obesity, Osteoarthritis, Mobility risk factors, Chronic Kidney Disease (CKD) Stage I, II, III or IV, Proteinuria, Struvite urolith dissolution, Struvite urolith prevention, Calcium Oxalate urolith (CaOx) prevention, Calcium Phosphate urolith (CaP) prevention, Idiopathic cystitis, Poor skin and coat, Atopy, non-food related dermatopathies, Dental Calculus, Acute or chronic diarrhea, Acute or chronic vomiting, Gastritis, Enteritis, Colitis, Maldigestion, Malabsorption, Diabetes mellitus, Pancreatitis, Exocrine pancreatic insufficiency (EPI), and Hyperlipidemia. In certain embodiments, the animal is a dog and the one or more values indicative of the medical status of the animal are selected from the group consisting of Post weight loss, Overweight, Obesity, Osteoarthritis, Mobility risk factors, CKD Stage I, II, III or IV, Proteinuria, Struvite urolith dissolution, Struvite urolith prevention, Calcium Oxalate urolith (CaOx) prevention, Calcium Phosphate urolith (CaP) prevention, Idiopathic cystitis, Poor skin and coat, Atopy, non-food related dermatopathies, Dental Calculus, Acute or chronic diarrhea, Acute or chronic vomiting, Gastritis, Enteritis, Colitis, Maldigestion, Malabsorption, Diabetes mellitus, Pancreatitis, Exocrine pancreatic insufficiency (EPI), Hyperlipidemia, and Adverse food reaction.

In certain embodiments, the dry portion includes two distinct pre-made dry compositions selected from the group consisting of:

dry composition A with at least 1.5% of Sodium, at least 38% of protein and no more than 0% of fat, relative to the total weight of the composition on a dry-matter basis;

dry composition B with at least 0.5% of Psyllium Tegument, at least 35% of protein, at least 0.5% of calcium and no more than 0.7% of Phosphorus, relative to the total weight of the composition on a dry-matter basis;

dry composition C with at least 37% of protein, at least 1.5% of Sodium, at least 2.5% of chloride and at least 0.6% of EPA and/or DHA, relative to the total weight of the composition on a dry-matter basis;

dry composition D with at least 20% of TDF, at least 38% of protein, no more than 9% of fat and at least 1.3% of Potassium, relative to the total weight of the composition on a dry-matter basis;

dry composition E with at least 3.5% of linoleic acid, at least 0.4% of Phosphorus and no more than 7% of TDF, relative to the total weight of the composition on a dry-matter basis;

dry composition F with at least 0.55% of EPA and/or DHA, relative to the total weight of the composition on a dry-matter basis;

dry composition G with at least 0.8% of EPA/DHA and at least 1.5% of Sodium, relative to the total weight of the composition on a dry-matter basis;

dry composition H with at least 20% of fat, no more than 0.5% of Calcium and at least 5% of linoleic acid, relative to the total weight of the composition on a dry-matter basis;

dry composition I with at least 4% of Psyllium Tegument, relative to the total weight of the composition on a dry-matter basis;

dry composition J with no more than 6 ppm of total copper, relative to the total weight of the composition on a dry-matter basis;

dry composition A' with at least 1.7% of Sodium and no more than 10% of fat, relative to the total weight of the composition on a dry-matter basis;

dry composition B' with at least 40% of protein and at least 1.5% of calcium, relative to the total weight of the composition on a dry-matter basis;

dry composition C' with no more than 6% of fat, no more than 0.45% of Calcium and no more than 0.45% of Phosphorus, relative to the total weight of the composition on a dry-matter basis;

dry composition D' with at least 22% of fat, at least 0.55% of EPA and/or DHA and at least 5% of linoleic acid, relative to the total weight of the composition on a dry-matter basis;

dry composition E' with no more than 7% of fat, at least 25% of TDF and at least 35% of protein, relative to the total weight of the composition on a dry-matter basis;

dry composition F' with no more than 12% of protein, at least 22% of fat, at least 0.25% of phosphorus, no more than 0.5% of calcium and at least 0.7% of EPA and/or DHA, relative to the total weight of the composition on a dry-matter basis;

dry composition G' with no more than 0.35% of Calcium, no more than 0.35% of phosphorus, at least 1.6% of Sodium and at least 25% of TDF, relative to the total weight of the composition on a dry-matter basis;

dry composition H' with no more than 6% of fat and at least 1.6% of sodium, relative to the total weight of the composition on a dry-matter basis; and wherein none of the said pre-made dry compositions consists of a nutritionally complete composition;

dry composition I' with no more than 0.21% of Sodium and at least 1.65% of total arginine, relative to the total weight of the composition on a dry-matter basis;

dry composition J' with no more than 6 ppm of total copper and no more than 20% of fat, relative to the total weight of the composition on a dry-matter basis;

dry composition K' with at least 40% of protein and no more than 23% of starch, relative to the total weight of the composition on a dry-matter basis; and dry composition L' with at least 21% of total dietary fiber, relative to the total weight of the composition on a dry-matter basis.

In certain embodiments, the wet portion includes one pre-made wet composition selected from the group consisting of:

wet composition 1 with no more than 45 g/Mcal Crude fat, no more than 1.5 g/Mcal Phosphorus, at least 1.6 g/Mcal EPA+DHA, and at least 240 mg/Mcal Glucosamine+chondroitin;

wet composition 2 with at least 1.8 g/Mcal EPA+DHA, at least 240 mg/Mcal Glucosamine+chondroitin, at least 40 mg/Mcal Zinc, at least 37.5 mg/Mcal Vitamin B5, and at least 125 mg/Mcal Vitamin B3 (niacin);

wet composition 3 with at least 3 g/Mcal Sodium, at least 50 mg/Mcal L-Carnitine, at least 110 g/Mcal Protein, no more than 35 g/Mcal Crude Fat, at least Lactium® (milk protein hydrolysate), at least 0.98 g/Mcal Tryptophan, and at least 200% of the minimum NRC recommended amount in mg/Mcal in essential amino acids;

wet composition 4 with at least 50 mg/Mcal L-carnitine, at least 110 g/Mcal Protein, no more than 35 g/Mcal Crude Fat, at least 50 mg/Mcal Zinc, and at least 200% of the minimum NRC recommended amount in mg/Mcal in essential amino acids;

wet composition 5 with at least 1.8 g/Mcal of EPA+DHA, at least 80% of moisture in the finish product, at least 0.26 g/Mcal Lactium® (milk protein hydrolysate), at least 0.98 g/MCal tryptophan, and no more than 1.7 g/Mcal Phosphorus;

wet composition 6 with at least 9.3 g/Mcal Linoleic acid (LA), at least Alpha-linoleic acid (ALA), at least 37.5 mg/Mcal Vitamin B5, and at least 125 mg/Mcal Vitamin B3 (niacin);

wet composition 7 with no more than 67 g/Mcal Protein, no more than 1 g/Mcal Phosphorus, at least 1.7 g/Mcal Potassium, at least 1 g/Mcal EPA+DHA, at least 9.3 g/Mcal Linoleic acid (LA), and at least 0.42 g/Mcal Alpha-linoleic acid (ALA);

wet composition 8 with at least 1.5 g/Mcal EPA+DHA, at least 200 mg/Mcal Glucosamine+Chondroitin, no more than 1.5 g/Mcal Phosphorus, at least 9.3 g/Mcal Linoleic acid (LA), and at least 0.42 g/Mcal Alpha-linoleic acid (ALA);

wet composition 9 with at least 1 g/Mcal EPA+DHA, no more than 1.7 g/Mcal phosphorus at least 7.6 g/Mcal Linoleic acid (LA), and at least 0.42 g/Mcal Alpha-linoleic acid (ALA); and wet composition 10 with no more than 35 g/Mcal Crude Fat, at least 6 g/Mcal Linoleic acid (LA), at least 1 g/Mcal EPA+DHA, and no more than 1.7 g/Mcal Phosphorus.

In certain embodiments, the present disclosure provides one or more computer-readable non-transitory storage media storing instructions operable when executed by one or more processors to cause performance of:

digitally storing composition data specifying a plurality of pre-made wet compositions and a plurality of pre-made dry compositions;

receiving one or more values indicative of a physiological status of an animal;

programmatically generating and digitally storing an individual general profile of the animal by inferring, at least partly based on the one or more values, an individual physiological profile of the animal;

programmatically determining, at least partly based on the individual general profile of the animal, a nutrient requirement (NR), a maintenance energy requirement (MER), and a wet-dry ratio (WDR);

programmatically selecting, at least partly based on the NR, one of the pre-made wet compositions and at least two of the pre-made dry compositions, the at least two of the pre-made dry compositions being distinct;

programmatically determining, at least partly based on the MER and the WDR, a fixed amount of the pre-made wet composition to obtain a wet portion of a nutritionally complete mix diet;

programmatically determining, at least partly based on the MER, the WDR, and the fixed amount of the pre-made wet composition, an adjusted amount of each of the at least two pre-made dry compositions to obtain a dry portion of the nutritionally complete mixed diet; and causing displaying, in a graphical user interface, a representation of the nutritionally complete mixed diet, the representation indicating the wet portion and the dry portion.

In certain embodiments, the present disclosure provides a system including one or more processors, and one or more computer-readable non-transitory storage media coupled to one or more of the processors and storing instructions operable when executed by one or more of the processors to cause the system to perform operations including: digitally storing composition data specifying a plurality of pre-made wet compositions and a plurality of pre-made dry compositions, receiving one or more values indicative of a physiological status of an animal, programmatically generating and digitally storing an individual general profile of the animal by inferring, at least partly based on the one or more values, an individual physiological profile of the animal, programmatically determining, at least partly based on the individual general profile of the animal, a nutrient requirement (NR), a maintenance energy requirement (MER), and a wet-dry ratio (WDR), programmatically selecting, at least partly based on the NR, one of the pre-made wet compositions and at least two of the pre-made dry compositions, the at least two of the pre-made dry compositions being distinct, programmatically determining, at least partly based on the MER and the WDR, a fixed amount of the pre-made wet composition to obtain a wet portion of a nutritionally complete mix diet, programmatically determining, at least partly based on the MER, the WDR, and the fixed amount of the pre-made wet composition, an adjusted amount of each of the at least two pre-made dry compositions to obtain a dry portion of the nutritionally complete mixed diet, and causing displaying, in a graphical user interface, a representation of the nutritionally complete mixed diet, the representation indicating the wet portion and the dry portion.

It is to be understood that both the foregoing summary and the following description are exemplary and explanatory only and are not restrictive of the disclosed embodiments, as claimed.

DETAILED DESCRIPTION OF THE DISCLOSURE

The present disclosure provides a method for making an individualized mixed diet for animals, such as, e.g., companion animals with said diet having both wet and dry portions. Further, the present disclosure aims to provide animals that have one or more pathological condition(s) with an individualized mixed diet by determining the nutrient requirement (NR), maintenance energy requirement (MER) and wet-dry ratio (WDR) specific to the individual animal by generating an individual profile with the animal's physiological status, and optionally medical status.

In certain embodiments of the present disclosure, the dry portion includes at least two distinct pre-made dry compositions, each of which is selected from a set of 5 or more distinct pre-made dry compositions. None of the systems or methods described in the art specifically discloses an individualized mixed diet having pre-made dry compositions/ components, where none of the pre-made dry compositions/ components on their own constitute a nutritionally complete diet, and where the pre-made dry compositions/components are selected from a plurality of distinct pre-made dry compositions/components, such as a set of 5 or more distinct pre-made dry compositions/components.

Surprisingly, it has been found that the preparation of an individualized nutritionally complete mixed diet for an animal from a selection of pre-made dry compositions with a pre-made wet composition could provide several advantages, including, but not limited to:

the method can allow the personalization of a plurality of animal food compositions with only a minimal amount of pre-manufactured compositions, hence providing a more economical alternative to other methods;

it can also be well adapted to animals with one or several diagnosed or suspected pathological condition(s), for example, pets that are susceptible to certain types of disorders (i.e., pets belonging to a specific breed, or which have an antecedent for a specific set of disorders). More particularly, it can be well adapted to animals with several diagnosed or suspected pathological conditions;

it can be particularly well adapted to the current habit of pet owners who already use a combination of wet and dry food while providing good nutritional balance for each individual pet.

The premade dry compositions/components can be, for example but not by the way of limitation pre-made dry core components, and in particular kibbles, where none of the pre-made dry compositions/components on their own constitute a nutritionally complete diet.

The disclosed methods can also be suitable for the preparation of individualized nutritionally complete mixed diets for animals without any pathological condition.

The present disclosure manages to solve the problem of being able to offer an individualized nutritionally complete mixed diet to a companion animal suffering from several diagnosed or suspected pathologies, said solution being easily reduced to practice at an industrial scale. The solution is based on a completely new approach including the combination of i) manufacturing pre-made dry not nutritionally complete compositions designed in a perspective of offering the perfect nutrients composition only when mixed and ii) manufacturing pre-made wet nutritionally incomplete compositions.

In some aspects, the method described herein is not based on i) mixing only already existing nutritionally complete composition with, as a consequence, a limitation of the nutrient mix possibility due to the level of each nutrient necessary to have these composition nutritionally complete, nor ii) mixing on a case by case in an "artisanal" way each nutrient with, as a consequence, a limitation in the industrial scale and an excessive price.

For clarity and not by way of limitation, this detailed description is divided into the following sub-portions:
1. Definitions;
2. Method for Providing an Individualized Diet;
   2.1. Nutritionally Complete Diet;
   2.2. Individualized Profiles;
   2.3. Wet and Dry Compositions;
   2.4. Implementation;
3. Computer-Implemented Methods, System Architectures, and Devices; and
4. Kits.

1. Definitions

The terms used in this specification generally have their ordinary meanings in the art, within the context of this disclosure and in the specific context where each term is used. Certain terms are discussed below, or elsewhere in the specification, to provide additional guidance to the practitioner in describing the compositions and methods of the present disclosure and how to make and use them.

In the description herein, references to "embodiment," "an embodiment," "one non-limiting embodiment," "in various embodiments," etc., indicate that the embodiment(s) described can include a particular feature, structure, or characteristic, but every embodiment might not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

As used herein, the words "a" or "an," when used in conjunction with the term "comprising" or "containing" or "including" in the claims and/or the specification, can mean "one," but they are also consistent with the meaning of "one or more," "at least one," and/or "one or more than one". The terms "having," "including," "containing" and "comprising" are interchangeable, and one of skill in the art will recognize that these terms are open ended terms.

The term "about" or "approximately" means within an acceptable error range for the particular value as determined by one of ordinary skill in the art, which will depend in part on how the value is measured or determined, i.e., the limitations of the measurement system. For example, "about" can mean within three or more than three standard deviations, per the practice in the art. Alternatively, "about" can mean a range of up to 20%, preferably up to 10%, more preferably up to 5%, and more preferably still up to 1% of a given value. Also, particularly with respect to systems or processes, the term can mean within an order of magnitude, preferably within five-fold, and more preferably within two-fold, of a value.

Moreover, the terms "at least" and "less than" encompass the hereafter cited value. For example, "at least 6 ppm" has to be understood as also encompassing "6 ppm".

As used herein, "a set of two or more distinct pre-made composition", can include 2, 3, 4, 5, 6, 7, 8, 9, 10, 11, 12, 13, 14, 15, 16, 17, 18, 19, 20 or more than 20 distinct pre-made compositions.

As used herein, a "pre-made dry composition" refers to a dry composition which is suitable for food consumption by an animal, but which is not nutritionally complete, and which upon mixing or contact with one or more pre-made dry compositions, according to a nutrient formula specific to the said animal, can provide an individualized nutritionally complete, or nutritionally incomplete, food composition. Such pre-made dry compositions are characterized by the presence of more than one type of compound and/or component. In that sense, a pure isolated compound is not itself pre-made.

As used herein, a "pre-made wet composition" refers to a wet composition which is suitable for food consumption by an animal. In an embodiment, said pre-made wet composition is nutritionally complete. In another embodiment, said pre-made wet composition cannot be nutritionally complete, and which upon mixing or contact with one or more pre-made wet compositions, according to a nutrient formula specific to the said animal, can provide an individualized nutritionally complete, or non-nutritionally complete, food composition. Such pre-made wet compositions are characterized by the presence of more than one type of compound and/or component. In that sense, a pure isolated compound is not itself pre-made.

As used herein, the terms "food", "diet" or "foodstuff" designate a material containing protein, carbohydrate and/or fat, which can be used in the body of an organism to sustain growth, repair and vital processes and to furnish energy. Foods can also contain supplementary substances or additives, for example, minerals, vitamins and condiments (See Merriam-Webster's Collegiate Dictionary, 10th Edition, 1993).

As used herein, the terms "dry diet", "dry food" or "dry composition", usually relate to a diet, food or a composition with about 20% or less than about 20% of moisture content, relative to the total weight of the composition/food, of about 14% or less than about 14% of moisture content, relative to the total weight of the composition. In general, such dry diet, dry food or dry composition can even contain much less than about 14% of moisture content, relative to the total weight of the composition, such as from about 1 to about 14% of moisture content. Although this definition is not limited to one specific form of presentation, a dry diet, dry food or dry composition can be presented in the form of (biscuit-like) kibbles, and/or dry core components. For instance, dry compositions can be manufactured by mixing ingredients together and kneading to make consistent dough that can be cooked. The process of creating a dry pet food can usually be done by baking and/or extruding. The dough can be typically fed into a machine called an expander and/or extruder, which uses pressurized steam or hot water to cook the ingredients. While inside the extruder, the dough is under extreme pressure and high temperatures. The dough can then be pushed through a die (specifically sized and shaped hole) and then cut off using a knife. The puffed dough pieces are made into a dry product, such as a kibble, by passing it through a dryer so that moisture is dropped down to a defined target ensuring stability of the food until consumption. The product/kibble can then be sprayed with fats, oils, minerals, vitamins, natural extracts cocktail, flavors and optionally sealed into packages.

As used herein, the term "kibble" includes a particulate pellet like component of animal feeds, such as dog and cat feeds, typically having a moisture, or water, content of less than about 20% by weight, relative to the total weight of the kibble. Kibbles can range in texture from hard to soft. Kibbles can range in internal structure from expanded to dense. Kibbles can be formed by an extrusion process. For instance, a kibble can be formed from a core and a coating to form a kibble that is coated, also called a coated kibble. It should be understood that when the term "kibble" is used, it can refer to an uncoated kibble or a coated kibble.

As used herein, the term "coating" means a partial or complete covering, typically on a core, that covers at least a portion of a surface, for example a surface of a core. In one example, a core can be partially covered with a coating such that only part of the core is covered, and part of the core is not covered and is thus exposed. In another example, the core can be completely covered with a coating such that the entire core is covered and thus not exposed. Therefore, a coating can cover from a negligible amount up to the entire surface. A coating can also be coated onto other coatings such that a layering of coatings can be present.

As used herein, the term "core component", such as in "dry core component", or "dry coated kibble" refers to an animal food product with a core and a shell at least partially covering said core. Hence the "core component" refers to the part of such an animal food product. Examples of such core components are described in U.S. Patent Application No. 2007/0020355, the entirety of which is incorporated herein by reference. Such dry core-components are particularly suitable as dry compositions, in the context of the present disclosure.

As used herein, the term "core", or "core matrix", means the particulate pellet of a kibble and is typically formed from a core matrix of ingredients and has a moisture, or water, content of less than about 12% by weight. The particulate pellet can be coated to form a coating on a core, which can be a coated kibble. The core can be without a coating or can be with a partial coating. In an embodiment without a coating, the particulate pellet can comprise the entire kibble. Cores can comprise farinaceous material, proteinaceous material, and mixtures and combinations thereof, such as those selected from a protein source, a carbohydrate source, and a fat source.

As used herein, the terms "wet diet", "wet food" or "wet composition", usually relate to a diet, food or a composition having a moisture content of about 30% or more, generally of more than about 40% by weight, and still more generally greater than about 60% relative to the total weight of the food composition. In some embodiments, the wet food composition can have a moisture content lower than about 90% in weight, relative to the total weight of the food composition. In general, it is the final product of a process having a final step of sterilization (instead of a drying step). In some embodiments, the wet food can be in chunk form, such as chunks in gravy. In some embodiments, the wet food can be chunks and gravy, chunks in jelly, loaf, mousse, terrine, bites form. "Chunks and gravy" products can have a preformed meat particle prepared by making a meat emulsion and by putting this meat emulsion through a muzzle under pressure and then cooked. A product, such as cooked meat, can be diced into chunks, which are eventually mixed with a gravy or sauce. The two components can then be filled into a container, usually a can or pouch, which can be seamed or sealed and sterilized. As opposed to the ground loaf, chunk and gravy compositions can have physically separated, discrete chunks (i.e., pieces of ground meat and grains) as prepared. These discrete particles can be present in the gravy-type liquid in the final container. When serving, chunk and gravy products flow out of the can and can be easily mixed with other dry products. Wet food compositions can be packaged in can-like containers or pouches and are considered "wet" in appearance because of the moisture contained therein. Two types of wet compositions are generally known in the art. The first is known in the art as "ground loaf" Loaf products can be typically prepared by contacting a mixture of components under heat to produce an essentially homogeneous, intracellular honeycomb-type mass or "ground loaf" The ground loaf mass can then be packaged into a cylindrical container, such as a can or in a pouch. Upon packing, ground loaf assumes the shape of the container such that the ground loaf is generally cut when serving to a companion animal. The wet food composition can be packaged. The packaging can be metal, plastic, paper, or card.

As used herein, the term "nutritionally complete" designates a composition, diet, or foodstuff that provides the complete and balanced nutritional requirements to the target animal (i.e., the companion animal or pet). For instance, such a nutritionally complete diet or composition can be a complete dog or a complete cat food. A nutritionally complete dry diet or composition is a nutritionally adequate feed with which the pet animal, e.g., a dog, can be fed as a daily ration, i.e., which is capable of sustaining life without additional food, except water. Illustratively, a nutritionally complete food diet or composition can include, in a non-exclusive manner, cereals and vegetable protein extracts, fibers, oils and fats, proteins, chicory pulps, yeasts and parts thereof, minerals, vitamins, preservatives, antioxidants, water, amino-acids, and sodium. In a general manner, nutritionally complete compositions can include at least one source of proteins (or polypeptides or amino-acids), such as, without limitation, protein extracts, at least one source of vitamins, at least one source of fats (or fatty acids) and at least one source of minerals.

In some embodiments, a nutritionally complete diet or composition can include at least one source of proteins (or polypeptides), such as, without limitation, protein extracts, at least one source of vitamins and at least one source of fats and at least one source of minerals, in minimal recommended amounts, such as those defined in Table 1A or 1B.

Examples of complete and balanced food are known in the art, such as those described in National Research Council, 1985, Nutritional Requirements for Dogs, National Academy Press, Washington D.C., or Association of American Feed Control Officials, Official Publication 1996, the disclosure of each of which is incorporated by reference herein.

Such complete diet or pet food can be defined according to the European Union (EU) Regulation no 767/2009, on placing on the market and the use of feed (art. 3(i)) adapted to pet food. If a manufacturer labels a product as a complete pet food without specification of a determined life stage, it is assumed to be complete for all life stages, and should be formulated according to the levels recommended (i.e., for early growth and reproduction). If the product is designed for a specific life stage, then the label must clearly state this.

In some embodiments, a nutritionally complete diet or composition can include a diet or a composition with at least one source of proteins, at least one source of vitamins, at least one source of fats and at least one source of minerals.

As used herein, a "mixed diet" refers to a diet having both dry food and wet food.

As used herein, a "daily ration" represents the average total quantity of feeding stuffs, calculated on a moisture content of about 12%, required daily by an animal of a given species, age category and yield, to satisfy all its needs. The above-mentioned legal definition means that the average total quantity of a specific pet food that is needed daily by a pet of a given species, age category and life style or activity to satisfy all its energy and nutrient requirements; also by reference to EU regulation no 767/2009 and use of feed (art. 2(c)).

As used herein, a "complementary pet food', also by reference to EU regulation no 767/2009 and use of feed (art. 3(j)) adapted to pet food, can be a pet food which has a high content of certain substances but which, by reason of its composition, is sufficient for a daily ration only if used in combination with other pet foods.

As used herein, an "allowance" or "recommendation" for daily intake (RDI) is the level of intake of a nutrient or food component that appears to be adequate to meet the known nutritional needs of practically all healthy individuals. It reflects the minimum requirement plus a safety margin for differences in availability between individual animals and for nutrient interactions. In practice this would be translated as the levels of essential nutrients that healthy individuals should consume over time to ensure adequate and safe nutrition.

As used herein, a "nutrient requirement", "nutrient requirements," or "NR" is the quantity of a nutrient that must be supplied to an animal in order to satisfy its metabolic needs. It reflects the minimum average level of intake of a nutrient, which, over time, is sufficient to maintain the desired biochemical physiological functions in a population.

As used herein, a "nutritional maximum limit" is the maximum level of a nutrient in a complete pet food that, based on scientific data, has not been associated with adverse effects in healthy pets, in particular healthy dogs and cats according to the European Pet Food Industry Federation Guidelines. In addition, maximum permitted levels have been determined by the legislator for several nutrients if added as a nutritional additive (i.e., trace elements & vitamin D) (legal maximum). They are laid down in the Community Register of Feed Additives pursuant to Regulation 1831/2002/ EC of the Parliament and the Council, concerning additives in feeding stuffs. The legal maximum levels apply to all life stages (EU Regulation 1831/2003 in conjunction with EU register of feed additives).

As used herein, the term "fat" encompasses any food-acceptable fat(s) and/or oil(s) irrespective of their consistency at room temperature, i.e., irrespective of whether said "fat" is present in essentially fluid form or in essentially solid form. The composition according to the disclosure can include fat of animal and/or vegetable origin. Fat can be supplied by any variety of sources known by those skilled in the art. Plant fat sources include, without limitation, wheat, sunflower, safflower, rapeseed, olive, borage, flaxseed, peanuts, blackcurrant seed, cottonseed, wheat, germ, corn germ, algae oil as well as oils derived from these and other plant fat sources. Animal sources include, for example and without limitation, chicken fat, turkey fat, beef fat, duck fat, pork fat, lamb fat, etc., fish oil, krill oil or any meat, meat by-products, seafood, dairy, eggs, etc. Fat content of foods can be determined by any number of methods known by those of skill in the art. A fat source can include, or even consist essentially of a mixture of fatty acids.

As used herein, the term "EPA and/or DHA" designates a fatty acid or a mixture of fatty acids consisting of (i) only eicosapentaenoic acid or its derivatives, such as its ester derivatives, such as eicosapentaenoic acid ethyl ester, and salts thereof (EPA), (ii) only docosahexaenoic acid or its derivatives, such as its ester derivatives, such as docosahexaenoic acid ethyl ester, and salts thereof (DHA) or (iii) a combination of eicosapentaenoic acid and docosahexaenoic acid, or their respective derivatives, such as eicosapentaenoic acid ethyl ester and docosahexaenoic acid ethyl ester, and salts thereof (EPA+DHA). Thus, an amount of "EPA and/or DHA" means (i) an amount of EPA, in the absence of DHA, (ii) an amount of DHA, in the absence of EPA, or (iii) an amount of a combination of EPA and DHA.

As used herein, the term "carbohydrates" designates a mixture of polysaccharides and sugars that are metabolized for energy when hydrolyzed in the body. The carbohydrate content of foods can be determined by any number of methods known by those skilled in the art. Carbohydrates can be supplied under the form of any of a variety of carbohydrate sources known by those skilled in the art, including without limitation starch (for example, any kinds, corn, wheat, barley, or the like), beet pulp (which can contain a small amount of sugars), and psyllium.

As used herein, the term "fiber", "dietary fiber", "total dietary fiber", or "TDF" (for "Total Dietary Fibers"), designates soluble fibers and insoluble fibers. Soluble fibers can be defined as being resistant to digestion and absorption in the small intestine and undergo complete or partial fermentation in the large intestine by opposition to insoluble fiber that can be defined as non-starch polysaccharides that are resistant to digestion and absorption in the small intestine, and resistant to fermentation in the large intestine. Soluble fibers are considered as having a prebiotic effect by providing short chain fatty acids as a source of energy to colonocytes. Insoluble fibers are considered as useful for transit and ballast effect. As non-limitative example of fibers, it can be mentioned a first group including beet pulp, guar gum, chicory root, psyllium, pectin, blueberry, cranberry, squash, apples, oats, beans, citrus, barley, or peas, and a second group including cellulose, whole wheat products, wheat oat, corn bran, flax seed, grapes, celery, green beans, cauliflower, potato skins, fruit skins, vegetable skins, peanut hulls, and soy fiber. In some embodiments, fiber is chicory pulp or cellulose.

As used herein, the term "psyllium" refers to a small seed produced by plants of the genus *Plantago*, principally *Plantago ovata* and *Plantago afra* and extracts thereof. Psyllium seeds are very rich in soluble and insoluble fibers (65% cellulose, hemicellulose and lignin, on the one hand, and 35% of gums, pectins and mucilage on the other). These fibers can be found mainly in the tegument or seed "husk".

As used herein, the term "starch" refers to a polysaccharide that is composed of amylose and amylopectin. Starch occurs in many plant tissues as granules, usually between 1 and 100 μm in diameter, depending upon the plant source. Chemically, starches are polysaccharides composed of α-D-glucopyranosyl units linked together with α-D(1-4) and/or α-D(1-6) linkages and are comprised of two molecular types: amylose, the straight chain polyglucan comprised of approximately 1000 α-D(1-4) linked glucoses; and amylopectin, the branched glucan, comprised of approximately 4000 glucose units with branches occurring as α-D(1-6) linkages. Starch encompasses the various crystalline structures of A-type, B-type, and C-type starches, which contain different proportions of amylopectin. A-type starches are found mainly in cereals, while B-type starches are found mainly in tubers and amylose-rich starches. C-type starch consists of a mixture of both A and B forms and is found mainly in legumes.

As used herein, the term "adult" means an animal that has passed puberty and has reached its biological maturation point.

As used herein, a "pet animal" or "companion animal" generally includes, or even consists of, a pet mammal. Pet mammals encompass dogs, cats, rabbits, hamsters, guinea pigs, rats, and mice. Certain non-limiting examples of pet animals referred to herein are feline or canine, especially as dogs and cats.

As used herein, the term "feline" encompasses animals, including pet animals, selected from cheetah, puma, jaguar, leopard, lion, lynx, liger, tiger, panther, bobcat, ocelot, smilodon, caracal, serval, and cats. As used herein, cats encompass wild cats and domestic cats, and in particular domestic cats.

As used herein, the term "canine" encompasses animals, including pet animals selected from recognized dog breeds (some of which are further subdivided), which can include afghan hound, airedale, akita, Alaskan malamute, basset hound, beagle, Belgian shepherd, bloodhound, border collie, border terrier, borzoi, boxer, bulldog, bull terrier, cairn terrier, chihuahua, chow, cocker spaniel, collie, corgi, dachshund, dalmatian, doberman, English setter, fox terrier, German shepherd, golden retriever, great dane, greyhound, griffon bruxellois, Irish setter, Irish wolfhound, King Charles spaniel, Labrador retriever, lhasa apso, mastiff, newfoundland, old English sheepdog, papillion, pekingese, pointer, pomeranian, poodle, pug, rottweiler, St. Bernard, saluki, samoyed, schnauzer, Scottish terrier, Shetland sheepdog, shih tzu, Siberian husky, Skye terrier, springer spaniel, West Highland terrier, whippet, Yorkshire terrier, etc.

As used herein, a "subpopulation" herein is a set of one to many animals of one species, but less than an entire species, definable in terms of genotype and/or one or more attributes of physiological condition that, in a subpopulation of more than one member, are common to members of the subpopulation. In certain embodiments, the subpopulation can be defined at least in part by specific breed. For example, in the case of animals of mixed breed, a subpopulation can be defined at least in part by breed heritage, which can be established through knowledge of the parental breeds, phenotypic characteristics, genotypic assessment, or by genetic markers such as SNPs. In certain embodiments, the subpopulation can be defined at least in part by physiological condition.

As used herein, the terms "physiological profile" refers to any one or combination of attributes of an animal including, without limitation, its species, breed, sex, neuter status, size, weight, age, activity level, disposition, state of wellness and medical history. A physiological profile is a product of interaction of the genotype with the environment of the animal. A subpopulation defined at least in part by physiological profile can cut across breed lines. Alternatively, a subpopulation can be defined in part by physiological condition but restricted to one or a few breeds or a defined breed heritage. Examples of such subpopulations are aggressive poodles, Labrador retrievers with tapeworm infestation, spayed female dogs having a breed heritage that includes beagle, etc.

As used herein, the term "pathological profile" or "medical profile" refers to any one or combination of attributes including an indication for a set of pathological conditions which have been associated to a given animal, or which are suspected to be present in said animal. For example, a subpopulation can include adult cats that shed hair excessively, obese dogs, toy dogs having respiratory disease, geriatric dogs of large breed type, long-haired cats having renal insufficiency, etc.

As used herein, the term "general profile" encompasses the physiological profile and the pathological profile.

As used herein the "ideal body weight" refers to the measured mass of the animal or the ideal mass of the animal as defined in a unit of weight such as kilograms or pounds. The BCS (body condition score) is a measure of the animal based on the shape of the animal's body from a visual assessment from the side and from above the animal when in a standing position. The BCS assessment can also include a tactile assessment using one's hands to feel the level of the fat mass over the animal's ribs (assessment based on how easily or difficult to palpate the ribs).The BCS refers to a score on a scale which typically ranges from 1 to 5, or 1 to 9. In some embodiments, the Body Condition Score can relate to the 1 to 9 scale, with a score of 5 being an ideal body weight.

As used herein, the term "biological sample" can refer to, but is not limited to, at least one of stool, urine, hair, blood, saliva, and tissue. Indeed, the term, "biological sample" refers not only to the biological material itself (proteins, nucleic acids, tissues, etc.) but also to other materials associated therewith used for detection of the biological material, or portions thereof (e.g., dyes, labels, stains, or any other marker used in the identification of materials).

As used herein, "biological material" refers to, for example, a sample of tissue or fluid isolated from a subject, including but not limited to, for example, blood, plasma, serum, fecal matter, urine, bone marrow, bile, spinal fluid, lymph tissue and lymph fluid, samples of the skin, external secretions of the skin, respiratory, intestinal, and genitourinary tracts, tears, saliva, milk, blood cells, organs, biopsies and also samples of in vitro cell culture constituents including but not limited to conditioned media resulting from the growth of cells and tissues in culture medium, e.g., recombinant cells, and cell components. A biological sample can include, for instance, a polypeptide or a polynucleotide, or fragmented portions of organisms or cells obtained from sampling the environment, such as airborne pathogens.

"Polypeptide" as used herein refers to a polymer of amino acids and does not refer to a specific length of a polymer of amino acids. Thus, for example, the terms peptide, oligopeptide, protein, and enzyme are included within the definition of polypeptide. This term also includes post-expression modifications of the polypeptide, for example, glycosylations, acetylations, phosphorylations and the like.

Also, as used herein, the term "polynucleotide" refers to a polymeric form of nucleotides of any length, either ribonucleotides or deoxynucleotides, and includes both double- and single-stranded DNA and RNA. A polynucleotide can include nucleotide sequences having different functions, including for instance coding sequences, and non-coding sequences such as regulatory sequences. A polynucleotide can be obtained directly from a natural source, or can be prepared with the aid of recombinant, enzymatic, or chemical techniques. A polynucleotide can be linear or circular in topology. A polynucleotide can be, for example, a portion of a vector, such as an expression or cloning vector, or a fragment.

As used herein, an amount of a component as expressed as weight/Mcal refers to a weight amount of the said component by unit of Metabolizable Energy (ME) of the total food composition. As used herein, the "Metabolizable Energy (ME)" refers to the digestible energy minus the energy lost in urine and combustible gases.

As used herein the "maintenance energy requirement", "maintenance energy requirements" or "MER" is the energy required to support energy equilibrium, where ME equals heat production, over a long period of time.

Illustratively, the ME value can be measured using feeding trial. In practice, the gross energy (GE) of the food is determined in the laboratory, and the amounts of food eaten by the animals are recorded. The feces and urine from the animals are collected, and the energy in each is determined and called fecal energy (FE) and urinary energy (UE), respectively. The ME is then calculated as:

$$ME(kcal/Kg)=[GE-(FE+UE)]/Kg \text{ of food consumed.}$$

Metabolizable Energy is conventionally determinable according to standard methods, and especially according to the European Standard EN 16967 (ICS.65.120) dated of July 2017 and incorporated herein by reference. Hence, as used herein, the term "x g/Mcal" for a given substance comprised in a diet or foodstuff means that the said substance is in an amount of x grams per Mcal contained in the said diet of foodstuff.

For dry products, assuming an energy density of 16.7 kJ (4 kcal) ME per gram of dry matter, the following conversion factors can apply:

$$\text{Units/100 g of dry matter} \times 2.5 = \text{units/1000 kcal}$$

For wet product, the moisture being a lot more variable (typically from 60% up to or even 90%), it is more difficult to assume a simple equivalence between units/100 g dry matter and units/1000 kcal. It requires knowing the energy (ME) of the diet, expressed in kcal/kg of finish product using NRC 2006 TDF equation, and the dry matter content, expressed in g dry matter per 100 g of finish product:

$$\text{Unit per 100 g dry matter}=[(\text{unit per 1000 kcal*ME in kcal/kg of finish product})/(\text{dry matter per 100 g of finish product*100})]$$

or $$\text{Unit per 1000 kcal}=[(\text{unit per 100 g dry matter*dry matter per 100 g of finish product*100})/\text{ME in kcal/kg of finish product}]$$

As used herein, the term "wet-dry ratio" or "WDR" refers to the ratio of energy coming from the wet portion to energy coming from the dry portion. As an example, a WDR expressed as 40:60 means that approximatively 40% of the energy is coming from the wet portion and the remaining 60% of the energy is coming from the dry portion.

As used herein, the term "ppm" or "ppm units" (also termed "parts per million"), is another conventional way of specifying an amount of a substance comprised in a composition or a diet.

As used herein, the term "sequential" or "sequentially" means that information is input in a successive manner such that a first portion of information is input at a first time, a second portion of information is input at a second time subsequent to the first time, and so on. The time between sequential inputs can be, for example, one or several days, weeks, months, or the like.

As used herein, the term "user" includes, for example, a person or entity that owns a computing device or wireless device; a person or entity that operates or utilizes a computing device or a wireless device; or a person or entity that is otherwise associated with a computing device or wireless device. For instance, the term "user" can be used to refer to any type of individual consumer, customer, researcher and/or the like that receives and/or transmits information from/to a user interface. Users include, but are not limited to, pet owners, veterinarians, manufacturers, organizations, wholesalers, vendors, members and/or the like. It is contemplated that the term "user" is not intended to be limiting and can include various examples beyond those described.

As used herein, the term "reference database" means the proprietary set of growth references, charts, data points, graphs, media, code, and information for animals of specific sex, breed, and/or size, among other measurable factors.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing" or "computing" or "calculating" or "determining" or "displaying" or "analyzing" or the like, can be achieved through the action and processes of a computer system, or similar electronic computing device, that manipulates and transforms data represented as physical (electronic) quantities within the computer system's registers and memories into other data similarly represented as physical quantities within the computer system memories or registers or other such information storage, transmission, or display devices.

2. Methods for Providing an Individualized Diet

The presently disclosed subject matter provides for methods of providing individualized diets to animals, based on their physiological profile. Such methods include identification of a nutritionally complete diet, based on individualized profiles, use of wet and dry compositions, and the implementation of combining the wet and dry compositions. Each of these aspects is discussed in further detail below.

In certain embodiments, the present disclosure relates to a method for providing an individualized nutritionally complete mixed diet for an animal, in particular an animal with one or more pathological condition(s), with said diet including a wet portion containing one pre-made wet composition combined with a dry portion containing at least two (2) pre-made dry compositions, the method including the steps of:

a) providing an individual physiological profile of an animal, and optionally an individual pathological profile of the animal, from one or more values indicative of a physiological status, and optionally from a medical status, of the said animal, whereby an individual general profile is generated;

b) processing the individual general profile, to determine a nutrient requirement (NR), a maintenance energy requirement (MER), and a wet-dry ratio (WDR) specific to the animal;

c) selecting, based on the NR, one pre-made wet composition from a plurality of distinct pre-made wet compositions, and at least two distinct pre-made dry compositions from a plurality of distinct pre-made dry compositions;

d) determining, based on the MER and the WDR, a fixed amount of the pre-made wet composition to obtain the wet portion of the nutritionally complete mixed diet;

e) determining, based on the MER, the WDR and the fixed amount of the pre-made wet composition, an adjusted amount of each of the at least two distinct pre-made dry compositions to obtain the dry portion of the nutritionally complete mixed diet;

f) combining the wet portion and the dry portion to obtain a nutritionally complete mixed diet, wherein none of the selected distinct pre-made dry compositions is a nutritionally complete diet on its own.

It must be understood that the methods described herein represent certain particular embodiments of the disclosure and that equivalent methods based on the same general principle should be considered as within the scope of the present disclosure.

In some embodiments, said nutritionally complete mixed diet can be defined as including at least one source of proteins, at least one source of vitamins, at least one source of fats and at least one source of minerals.

2.1 Nutritionally Complete Diet

In certain embodiments, the present disclosure relates to an individualized nutritionally complete mixed diet which can be obtained by the method described herein. In certain embodiments, the nutritionally complete mixed animal diet can be an animal diet including nutrient levels at least at the minimum recommended allowances for commercial compositions and at least below the maximum recommended allowances for commercial compositions.

According to certain embodiments, an animal food diet or composition which is not nutritionally complete, according to the present disclosure, is an animal food diet or composition, which includes one or more nutrient levels below the minimum recommended allowances for commercial compositions or an animal food diet or composition, which includes one or more nutrient levels higher than the maximum recommended allowances for commercial compositions.

According to certain other embodiments, an animal food diet or composition which is not nutritionally complete, according to the present disclosure, can refer to an animal diet or composition including a plurality of nutrient levels below the minimum recommended allowances for commercial compositions or to animal diets or compositions including one or more nutrient levels higher than the maximum recommended allowances for commercial compositions.

For reference, the recommended nutrient levels for dogs, as expressed in units per 100 g of dry matter (DM) are indicated in Table 1A here below:

TABLE 1A recommended nutrient levels for dogs

| Nutrient | Unit | Minimum Recommended Adult-based on MER of 95 Kcal/kg % DM | Maximum Recommended % DM |
|---|---|---|---|
| Protein | % | 21 | |
| Arginine | % | 0.6 | |
| Histidine | % | 0.27 | |
| Isoleucine | % | 0.53 | |
| Leucine | % | 0.95 | |
| Lysine | % | 0.46 | |
| Methionine | % | 0.46 | |
| Methionine + Cysteine | % | 0.88 | |
| Phenylalanine | % | 0.63 | |
| Phenylalanine + Tyrosine | % | 1.03 | |
| Threonine | % | 0.6 | |
| Tryptophan | % | 0.2 | |
| Valine | % | 0.68 | |
| Fat | % | 5.5 | |
| Linoleic acid (ω-6) | % | 1.53 | |
| Arachidonic acid (ω-6) | mg/kg | — | |
| Alpha-linolenic acid (ω-3) | % | | |
| EPA + DHA (ω-3) | % | | |

TABLE 1A-continued recommended nutrient levels for dogs

| Nutrient | Unit | Minimum Recommended Adult-based on MER of 95 Kcal/kg % DM | Maximum Recommended % DM |
|---|---|---|---|
| Minerals | | | |
| Calcium/Phosphorus | ratio | 1 | 2 |
| Calcium | % | 0.58 | 2.5 |
| Phosphorus | % | 0.46 | |
| Potassium | % | 0.58 | |
| Sodium | % | 0.12 | |
| Chloride | % | 0.17 | 2.35 |
| Magnesium | % | 0.08 | |
| Trace elements | | | |
| Copper | ppm | 8.3 | 28 |
| Iodine | ppm | 1.2 | 11 |
| Iron | ppm | 41.7 | 1420 |
| Manganese | ppm | 6.7 | 170 |
| Selenium | ppm | 0.35 | 0.56 |
| Zinc | ppm | 83 | 227 |
| Vitamins | | | |
| Vitamin A | IU/g | 7 | 400 |
| Vitamin D | IU/kg | 639 | 2270 |
| Vitamin E | ppm | 41.7 | |
| Thiamine | mg/kg | 0.25 | |
| Riboflavin | mg/kg | 0.69 | |
| Pantothenic acid | mg/kg | 1.64 | |
| Vitamin B6 (Pyridoxine) | mg/kg | 0.17 | |
| Vitamin B12 | µg/kg | 3.87 | |
| Niacin | mg/kg | 1.89 | |
| Folic acid | µg/kg | 29.9 | |
| Choline | mg/kg | 189 | |

For reference, the recommended nutrient levels for cats, as expressed in units per 100 g of dry matter (DM) are indicated in Table 1B here below:

TABLE 1B recommended nutrient levels for cats

| Nutrient | Unit | % of DM Adult-based on MER of 75 kcal/kg Minimum recommended | Maximum recommended |
|---|---|---|---|
| Protein | % | 33.3 | |
| Arginine | % | 1.3 | |
| Histidine | % | 0.35 | |
| Isoleucine | % | 0.57 | |
| Leucine | % | 1.36 | |
| Lysine | % | 0.45 | |
| Methionine | % | 0.23 | |
| Methionine + Cysteine | % | 0.45 | |
| Phenylalanine | % | 0.53 | |
| Phenylalanine + Tyrosine | % | 2.04 | |
| Threonine | % | 0.69 | |
| Tryptophan | % | 0.17 | |
| Valine | g | 0.68 | |
| Taurine | | 0.27 | |
| Fat | % | 9 | |
| Linoleic acid (ω-6) | % | 0.67 | |
| Arachidonic acid (ω-6) | mg/kg | 8 | |
| Alpha-linolenic acid (ω-3) | % | — | |
| EPA + DHA (ω-3) | % | — | |
| Minerals | | | |
| Calcium/Phosphorus | ratio | 1 | 2 |
| Calcium | % | 0.79 | |
| Phosphorus | % | 0.67 | |

TABLE 1B-continued recommended nutrient levels for cats

| Nutrient | Unit | % of DM Adult-based on MER of 75 kcal/kg | |
| | | Minimum recommended | Maximum recommended |
| --- | --- | --- | --- |
| Potassium | % | 0.8 | |
| Sodium | % | 0.1 | 1.5 |
| Chloride | % | 0.15 | 2.25 |
| Magnesium | % | 0.05 | |
| Trace elements | | | |
| Copper | ppm | 6.7 | 28 |
| Iodine | ppm | 1.7 | 11 |
| Iron | ppm | 107 | 1420 |
| Manganese | ppm | 6.7 | 170 |
| Selenium | ppm | 0.4 | 0.57 |
| Zinc | ppm | 100 | 200 |
| Vitamins | | | |
| Vitamin A | IU/g | 4.4 | 400 |
| Vitamin D | IU/kg | 333 | 2270 |
| Vitamin E | ppm | 50.7 | |
| Thiamine | ppm | 5.9 | |
| Riboflavin | mg/kg | 0.42 | |
| Pantothenic acid | mg/kg | 0.77 | |
| Vitamin B6 (Pyridoxine) | mg/kg | 0.33 | |
| Vitamin B12 | μg/kg | 2.35 | |
| Niacin | mg/kg | 4.21 | |
| Folic acid | μg/kg | 101 | |
| Biotin | μg/kg | 8 | |
| Choline | mg/kg | 320 | |

According to certain particular embodiments, a nutritionally complete pet food composition, such as a nutritionally complete dog food composition can be characterized by the presence of:

a protein content of at least about 18 g per 100 g of dry matter of the total composition;

a fat content of at least about 5.5 g per 100 g of dry matter of the total composition.

Conversely, the corresponding non-nutritionally complete pet (e.g., dog) food composition can be characterized by the presence of:

a protein content below about 18 g per 100 g of dry matter of the total composition; and/or a fat content below about 5.5 g per 100 g of dry matter of the total composition.

In certain embodiments, the protein content of a nutritionally complete dog food composition is from about 18 g to about 30 g, from about 18 g to about 25 g, from about 18 g to about 21 g, from about 20 g to about 25 g, from about 20 g to about 30 g, or about 21 g per 100 g of dry matter of the total composition.

In certain embodiments, the fat content of a nutritionally complete dog food composition is from about 5.5 g to about 15 g, from about 5.5 g to about 10 g, from about to about 7.5 g, from about 7.5 go to about 15 g, from about 7.5 g to about 10 g, or about per 100 g of dry matter of the total composition.

According to certain particular embodiments, a nutritionally complete pet food composition, such as a complete cat food composition can be characterized by the presence of:

a protein content of at least about 25 g per 100 g of dry matter of the total composition;

a fat content of at least about 9 g per 100 g of dry matter of the total composition.

Conversely, the corresponding non-nutritionally complete pet (e.g., cat) food composition can be characterized by the presence of:

a protein content below about 25 g per 100 g of dry matter of the total composition; and/or a fat content below about 9 g per 100 g of dry matter of the total composition.

In certain embodiments, the protein content of a nutritionally complete cat food composition is from about 25 g to about 40 g, from about 25 g to about 35 g, from about 25 g to about 30 g, from about 30 g to about 40 g, from about 35 g to about 40 g, or about 33 g per 100 g of dry matter of the total composition.

In certain embodiments, the fat content of a nutritionally complete cat food composition is from about 9 g to about 25 g, from about 9 g to about 20 g, from about 9 g to about 15 g, from about 15 go to about 25 g, from about 15 g to about 20 g, or about 9 g per 100 g of dry matter of the total composition.

The individualized nutritionally complete mixed diet, which can be obtained according to the method of the present disclosure is a nutritionally complete mixed composition, which can be in the form of foodstuff, which can encompass any product which a pet consumes in its diet. Thus, the present disclosure covers standard food products, wet and dry, as well as pet food snacks (for example, snack bars, biscuits, and sweet products). The individualized nutritionally complete mixed diet herein can be a cooked product. It can incorporate meat or animal derived material (such as a material derived from beef, chicken, turkey, pork, duck, kangaroo, lamb or fish, blood plasma, bone marrow, feather-derived material) (e.g., feather hydrolysate such as poultry feather hydrolysate) etc. The individualized nutritionally complete mixed diet alternatively can be meat free and can include a meat substitute such as soya, maize gluten or a soya hydrolysate in order to provide a protein source. The individualized nutritionally complete mixed diet can contain additional protein sources such as vegetal protein (wheat gluten, pea protein) or soya protein concentrate or hydrolysate, milk proteins, gluten etc. The individualized nutritionally complete mixed diet can also contain a starch source such as one or more grains (e.g., wheat, corn, rice, oats, barley, etc.), or carbohydrates coming from other sources such as potato or can be starch free. The individualized nutritionally complete mixed diet can include fiber such as chicory, sugar beet pulp, etc. and/or components such as inulin, fructooligosaccharides, and probiotics. In certain embodiments, the combined ingredients of the diet or foodstuff provide all the recommended vitamins and minerals for the particular animal in question (a complete and balanced food) for example as described in National Research Council, 1985, Nutritional Requirements for dogs, National Academy Press, Washington DC or Association of America Feed Control Officials, Official Publication 1996 (the content being incorporated herein by reference).

The dry portion of the nutritionally complete mixed diet or foodstuff can be manufactured by mixing ingredients together and kneading in order to make consistent dough or meat emulsion that can be cooked. The process of creating an embodiment of a dry portion can be usually done by baking and/or extruding. The dough can be typically fed into a machine called an expander and/or extruder, which uses pressurized steam or water to cook the ingredients. While inside the extruder, the dough is under extreme pressure and high temperatures. The dough can then be pushed through a die (specifically sized and shaped hole) and then cut off using a knife. The puffed dough pieces are made into kibble by passing it through a dryer so that moisture is dropped down to a defined target ensuring stability of the food until consumption. The dry portion (i.e., the kibble) can then be sprayed with fats, oils, minerals, vitamins, the natural extracts cocktail, palatants, and optionally sealed into packages.

The above-mentioned method can further include a step of mixing the adjusted amount of the at least two distinct pre-made dry compositions selected at step e), whereby the dry portion of the individualized nutritionally complete mixed diet is provided.

2.2 Individualized Profiles

The method of the present disclosure includes providing an individualized diet for animals. To individualize the diet for animals, such that they receive a nutritionally complete mixed diet, a general profile of the animal can be obtained. In certain embodiments, this profile can be prepared based on answers to questions pertaining to, but not limited to, an animal's name, species, age, weight, gender, breed, spayed/neutered, activity level, breeding status, digestive health, medical history and genetic information, current health status, body condition, feeding method, snack schedule and flavor preferences. Further, the animal profile can also include information regarding the season, date, or time of year.

According to certain other embodiments, the present disclosure relates to a method for providing an individualized nutritionally complete mixed diet for an animal, the method including a step a) providing an individual physiological profile of an animal from one or more values indicative of a physiological status of the said animal, whereby the individual general profile can be generated from the individual physiological profile.

According to certain other embodiments, the present disclosure relates to a method for providing an individualized nutritionally complete mixed diet for an animal with one or more pathological condition(s), the method including a step a) providing an individual medical profile of an animal from one or more values indicative of a medical status of the said animal, whereby the individual general profile can be generated from the individual medical profile.

According to certain other embodiments, the present disclosure relates to a method for providing an individualized nutritionally complete mixed diet for an animal with one or more pathological condition(s), the method including a step a) providing an individual physiological and an individual medical profile of an animal from one or more values indicative of a physiological and of a medical status of the said animal, whereby an individual general profile can be generated from the individual physiological and/or the individual medical profile.

According to certain embodiments, the method can include a step of providing an individual physiological profile of an animal from one or more values indicative of the general status of said animal, which are selected from animal's breed, age, actual weight, targeted weight, Body Condition Score (BCS), activity, lifestyle, sexual status, and gestation status.

According to some embodiments, the method can include a step of providing an individual pathological profile or medical profile of an animal from one or more values indicative of a medical status of said animal. In certain embodiments, the animal can have one or more pathological conditions.

In a non-limitative manner, the disorders/pathologies listed in the public VENOM DATABASE (venomcoding.org) or in the public AAHA (American Animal Hospital Association) listing from the Veterinary Terminology Services Laboratory (https://vtsl.vetmed.vt.edu/aaha/) can be considered for the establishment of a physiological or pathological profile. In some other non-limiting embodiments, the following set of disorders/pathologies can be considered for the establishment of a physiological or pathological profile:

TABLE 2

| disorders/pathologies for the establishment of a physiological or pathological profile | |
|---|---|
| Behavioral Disorders | Stress and Anxiety Related Disorders, Chronic Anxiety |
| Dermatological Disorders | Self-Induced Alopecia, Adverse Food Reactions (Afr), Adverse Food Reactions Suspicion, Atopic Dermatitis (Atopy), Dermatitis, Flea Bite Allergic Dermatitis, Pyoderma, Skin and Coat Disorders Wound Healing, Coat Color Disorder (Incl Red Coat Syndrome), Cutaneous Afr, Dermatosis, Hair Loss, Pyodermatitis |
| Endocrine Disorders | Diabetes Mellitus (Dm), Hypothyroidism, Diabetes Mellitus Type 1 (Absolute Insulin Deficiency), Diabetes Mellitus Type 2 (Relative Insulin Deficiency or Insulin Resistance), Hyperthyroidism, Thyroid Disorders |
| Food Intake Disorders | Anorexia, Dysrexia, Food Intake Disorders |
| Gastro-Intestinal Disorders | Acute Diarrhea, Acute Gastroenteritis, Acute Vomiting, Chronic Diarrhea, Chronic Enteropathy (Ce), Chronic Gastroenteritis, Chronic Vomiting, Constipation, Fibre Responsive Colitis (Including Stress Diarrhea), Gastrointestinal Afr, Gastrointestinal Condition Requiring High Fibre Content, Inflammatory Bowel Disease (Ibd), Intestinal Diseases, Lymphangiectasia, Maldigestion Malabsorption, Megacolon, Megaoesophagus, Perianal Fistula, Protein-Losing Enteropathy (Ple), Acute Colitis, Antibiotic Responsive Diarrhea (Ard), Chronic Colitis, Chronic Idiopathic Large Bowel Disease (Cilbd), Delayed Gastric Emptying, Feline Triaditis (Enteritis + Cholangiohepatitis + Pancreatitis), Food Responsive Diarrhea (Frd), Functional Colopathy, Gastric Dilatation Volvulus (Recurrence Prevention), Gastric Disorders, Gastritis, Obstipation, Oesophagial Disorders, Oesophagitis, Small Intestinal Bacterial Overgrowth (Sibo), Steroid (Or Immunosuppressant) Responsive Diarrhea (Srd Or Ird) |

TABLE 2-continued

| | disorders/pathologies for the establishment of a physiological or pathological profile |
| --- | --- |
| Heart Disorders | Cardiovascular Diseases, Congestive Heart Failure (Chf), Hypertrophic Cardiomyopathy (Hcm), Dilated Cardiomyopathy (Dcm), Chronic Valvular Heart Disease (Cvhd) |
| Liver Disorders | Cholangiohepatitis, Cholangitis, Copper Storage Disease, Feline Hepatic Lipidosis, Hepatic Encephalopathy, Liver Diseases, Acute Hepatitis, Chronic Hepatitis, Liver Failure, Portosystemic Shunt (Pss) |
| Oral Disorders | Periodontal Disease, Dental Plaque, Gingivitis, Oral Diseases, Tartar |
| Osteoarticular Disorders | Bone Disorders, Joint Disorders, Osteoarthritis, Osteo-Articular Disorders, Osteochondritis |
| Other | Regurgitation, Malnutrition, Food Intolerance (Including Gluten Intolerance), Hairball Management, Anemia, Hyperlipidemia (Fasting Hyperlipidemia), Neoplasia (Cancer), Neurologic Diseases, Convalescence, Hypertension, Sarcopenia |
| Pancreatic Disorders | Acute Pancreatitis, Chronic Pancreatitis, Exocrine Pancreatic Insufficiency (Epi), Pancreatic Disorders (Exocrine Pancreas), Chronic Pancreatitis (Mild Moderate), Chronic Pancreatitis (Severe) |
| Renal Disorders | Acute Kidney Injury (Aki), Azotemic Ckd Iris Stage 2, Azotemic Ckd Iris Stage 3, Azotemic Ckd Iris Stage 4, Ckd With Proteinuria, Early Ckd (Iris Stage 1), Chronic Kidney Disease (Ckd), Ckd Mineral Bone Disorder (Secondary Hyperparathyroidism), Ckd With Hypertension, Glomerulonephritis, Kidney Dysplasia, Polycystic Kidney Disease (Pkd), Protein-Losing Nephropathy (Pln) |
| Urinary Disorders | Feline Idiopathic Cystitis (Fic), Urinary Tract Infection (Uti), Urolithiasis Calcium Oxalate (Or Calcium Phosphate), Urolithiasis Cystine, Urolithiasis Struvite, Urolithiasis Urate (Or Xanthine), Hematuria, Incontinence, Proteinuria, Urinary Disorders, Urolithiasis Undetermined |
| Weight Disorders | Obesity, Overweight, Underweight, Cachexia, Obesity Bcs 7 (Out Of 9), Obesity Bcs 8 (Out Of 9), Obesity Bcs 9 (Out Of 9), Overweight Bcs 6 (Out Of 9), Underweight Bcs 1 (Out Of 9), Underweight Bcs 2 (Out Of 9), Underweight Bcs 3 (Out Of 9) |

In addition to the listed pathologies, a list of "sensitivities" can also be taken into consideration when providing an individual pathological profile. In certain embodiments, the "sensitivities" can include: weight gain, struvite urolithiasis, oxalate urolithiasis, cystine urolithiasis, xanthine urolithiasis, idiopathic cystitis, stress and/or anxiety, bone and/or joint conditions, skin and coat sensitivity, gastrointestinal sensitivity, tartar, being a fussy eater, prone to having hairballs, prone to cardiac conditions.

In certain non-limiting embodiments, the following set of animals can be considered for the establishment of a physiological or pathological profile: feline, canine, dogs, cats, rabbits, hamsters, guinea pigs, rats, and mice. In certain particular embodiments, the pet animals herein are felines or canines, such as dogs and cats. In certain non-limiting embodiments, when the animal is a feline, the following species can be considered for the establishment of a physiological or pathological profile: cheetah, puma, jaguar, leopard, lion, lynx, liger, tiger, panther, bobcat, ocelot, smilodon, caracal, serval and cats. As used herein, cats encompass wild cats and domestic cats. In certain particular embodiments, the cats are domestic cats. In certain non-limiting embodiments, when the animal is a canine, the following set of breeds can be considered for the establishment of a physiological or a pathological profile: afghan hound, airedale, akita, Alaskan malamute, basset hound, beagle, Belgian shepherd, bloodhound, border collie, border terrier, borzoi, boxer, bulldog, bull terrier, cairn terrier, chihuahua, chow, cocker spaniel, collie, corgi, dachshund, dalmatian, doberman, English setter, fox terrier, German shepherd, golden retriever, great dane, greyhound, griffon bruxellois, Irish setter, Irish wolfhound, King Charles spaniel, Labrador retriever, lhasa apso, mastiff, newfoundland, old English sheepdog, papillion, pekingese, pointer, pomeranian, poodle, pug, rottweiler, St. Bernard, saluki, samoyed, schnauzer, Scottish terrier, Shetland sheepdog, shih tzu, Siberian husky, Skye terrier, springer spaniel, West Highland terrier, whippet, Yorkshire terrier.

According to some embodiments, the method can include a step of providing an individual pathological profile of a pet; wherein the one or more values indicative of a medical status of the said pet can be selected from:

disorders associated to obesity and/or weight;
    food allergies;
    kidney disorders at an early stage;
    kidney disorders at a late stage;
    urinary disorders linked to calcium oxalate;
    urinary disorders linked to struvite;
    gastro-intestinal disorders;
    disorders linked to a fat-rich diet;
    skin disorders (i.e., dermatitis);
    dental disorders;
    age-related disorders;
    joint disorders.

According to some embodiments, the method can include a step of providing an individual pathological profile of a cat, wherein the one or more values indicative of a medical status of the said cat can be selected from:

disorders associated to obesity and/or weight;
    food allergies;

kidney disorders at an early stage;

kidney disorders at a late stage;

urinary disorders linked to calcium oxalate;

urinary disorders linked to struvite;

gastro-intestinal disorders;

disorders linked to a fat-rich diet;

skin disorders (i.e., dermatitis);

dental disorders;

age-related disorders.

According to some embodiments, the method can include a step of providing an individual pathological profile of a dog, wherein the one or more values indicative of a medical status of the said dog can be selected from:

disorders associated to obesity and/or weight;

kidney disorders at an early stage;

kidney disorders at a late stage;

urinary disorders linked to calcium oxalate;

urinary disorders linked to struvite;

gastro-intestinal disorders;

disorders linked to a fat-rich diet;

skin disorders (i.e., dermatitis);

dental disorders;

age-related disorders;

joint disorders.

Disorders associated with obesity and/or weight generally require a low-energy low-fat protein-rich and fiber-rich diet. Food allergies generally require a hypoallergenic diet. Kidney disorders at an early stage generally require a low-phosphorus diet. Kidney disorders at a late stage generally require a low-phosphorous and a low-protein diet. Urinary disorders linked to calcium oxalate generally require a sodium-rich diet without acidification. Urinary disorders linked to struvite generally require a sodium-rich diet with acidification. Gastro-intestinal disorders generally require a highly digestible protein source and a fiber-specific diet (including for instance psyllium). Disorders linked to a fat-rich diet generally require a fat-low diet. Skin disorders (e.g., dermatitis) generally require a vitamin B-rich and EPA/DHA rich diet. Dental disorders generally require a calcium-chelating diet.

According to some embodiments, the method can include a step of providing an individual physiological profile of a cat, and optionally an individual pathological profile of the cat; wherein the one or more values indicative of a medical status of the cat can be selected from post weight loss, overweight, obesity, osteoarthritis, mobility risk factors, chronic kidney disease (CKD) Stage I or II, CKD Stage III or IV, proteinuria, struvite urolith dissolution, struvite urolith prevention, calcium oxalate urolith (CaOx) prevention, calcium phosphate urolih (CaP) prevention, idiopathic cystitis, poor skin and coat, atopy, non-food related dermatopathies, dental calculus, acute or chronic diarrhea, acute or chronic vomiting, gastritis, enteritis, colitis, maldigestion, malabsorption, diabetes mellitus, pancreatitis, exocrine pancreatic insufficiency (EPI), and hyperlipidemia.

According to some embodiments, the method can include a step of providing an individual physiological profile of a dog, and optionally an individual pathological profile of the dog; wherein the one or more values indicative of a medical status of the said dog can be selected from post weight loss, overweight, obesity, osteoarthritis, mobility risk factors, CKD (chronic kidney disease) Stage I or II, CKD Stage III or IV, proteinuria, struvite urolith dissolution, struvite urolith prevention, calcium oxalate urolith (CaOx) prevention, calcium phosphate urolith (CaP) prevention, idiopathic cystitis, poor skin and coat, atopy, non-food related dermatopathies, dental calculus, acute or chronic diarrhea, acute or chronic vomiting, gastritis, enteritis, colitis, maldigestion, malabsorption, diabetes mellitus, pancreatitis, exocrine pancreatic insufficiency (EPI), hyperlipidemia, and adverse food reaction.

According to some embodiments, more than one nutrient formula specific to the said animal can be provided. For instance, two or more than two nutrient formulae can be provided. Such a situation can, for instance, occur when the individual general profile is generated from one or more values indicative of a physiological and/or medical status of the said animal, which when associated, lead to a plurality of antagonistic nutritional answers. In such a case, the method can require an additional step, referred herein as prioritization, which requires adaptation of the set of values indicative of physiological and/or medical profiles in a manner suitable to generate only a limited set (i.e., only one) of nutrient formulae specific to the said animal.

Hence, according to such an embodiment, the method of the disclosure for providing an individualized nutritionally complete mixed diet for an animal, in particular an animal with one or more pathological condition(s), said diet including a wet portion containing one pre-made wet composition combined with a dry portion containing at least two pre-made dry compositions, can include the steps of:

a) providing an individual physiological profile of an animal, and optionally an individual pathological profile of the animal, from one or more values indicative of a physiological status, and optionally of a medical status, of the said animal, whereby an individual general profile is generated from the individual physiological profile and optionally the individual pathological profile;

b) processing the individual general profile, and optionally discarding one or more of the values indicative of a physiological/or medical status which were provided in the preceding step, to determine a nutrient requirement (NR), a maintenance energy requirement (MER) and a wet-dry ratio (WDR) specific to the animal;

c) selecting, based on the NR, one pre-made wet composition from a plurality of pre-made wet compositions, and at least two distinct pre-made dry compositions from a plurality of distinct pre-made dry compositions, d) determining, based on the MER and the WDR, a fixed amount of the pre-made wet composition to obtain the wet portion of the nutritionally complete mix diet;

e) determining, based on the MER, the WDR, and the fixed amount of the pre-made wet composition, an adjusted amount of each of the at least two distinct pre-made dry compositions to obtain the dry portion of the nutritionally complete mixed diet, f) combining the wet portion and the dry portion to obtain a nutritionally complete mix diet, wherein none of the selected distinct pre-made dry compositions consists of a nutritionally complete diet on its own.

Alternatively, two or more nutrient requirements (NR) specific to the animal can be provided, and a selection of one optimal nutrient requirement (NR) can then be achieved through an additional step, referred herein as duplication. For instance, the step of selecting the individualized optimal nutrient requirement (NR) among the plurality can include discarding or ignoring one or more values indicative of the physiological and/or medical status of said animal based on user preference, so that only one individualized nutritionally complete mixed diet is finally provided.

According to some embodiments, the method of the disclosure for providing an individualized nutritionally complete mixed diet for an animal, in particular an animal with one or more pathological condition(s), can include the steps of:

a) providing an individual physiological profile of an animal, and optionally an individual pathological profile of the animal, from one or more values indicative of a physiological status, and optionally of a medical status, of the said animal, whereby an individual general profile is generated;

b) processing the individual general profile, to determine a plurality of nutrient requirement (NR), an energy maintenance requirement (MER), and a wet-dry ratio (WDR) specific to animal;

c) selecting, among the plurality of NR specific to the animal, one individualized optimal NR;

d) selecting, based on the optimal NR, one pre-made wet composition from a plurality of pre-made wet compositions, and at least two distinct pre-made dry compositions from a plurality of distinct pre-made dry compositions;

e) determining, based on the MER and the WDR, a fixed amount of the pre-made wet composition to obtain the wet portion of the nutritionally complete mix diet, f) determining, based on the MER, the WDR and the fixed amount of the pre-made wet composition, an adjusted amount of each of the at least two pre-made dry compositions to obtain the dry portion of the nutritionally complete mixed diet, g) combining the wet portion and the dry portion to obtain a nutritionally complete mix diet, wherein none of the selected distinct pre-made dry compositions consists of a nutritionally complete diet on its own. It will be understood herein that, according to the previous example, the step of selecting a nutrient requirement among a plurality within step c) can be achieved through an automatic procedure, or alternatively through manual input (i.e., through a particular user interface).

According to some embodiments, both duplication and prioritization can be achieved within a same sequence.

Hence, according to some embodiments, one or more of the values indicative of a general status can be discarded, and a plurality of optimal nutrient requirement can be generated.

According to some embodiments, the method described in the present disclosure for providing an individualized nutritionally complete mixed diet for an animal, in particular an animal with one or more pathological condition(s), can include the steps of:

a) providing an individual physiological profile of an animal, and optionally an individual pathological profile of the animal, from one or more values indicative of a physiological status, and optionally of a medical status, of the said animal, whereby an individual general profile is generated;

b) processing the individual general profile, and optionally discard one or more of the values indicative of a physiological and/or medical status which were provided in the preceding step, whereby a plurality of nutrient requirement (NR) specific to the animal is determined;

c) selecting, among the plurality of NR specific to the animal, one individualized optimal NR;

d) selecting, based on the individualized optimal NR, a pre-made wet composition from a plurality of pre-made wet compositions, and at least two distinct pre-made dry compositions from a plurality of distinct pre-made dry compositions;

e) determining, based on the MER and the WDR, a fixed amount of the pre-made wet composition to obtain the wet portion of the nutritionally complete mix diet;

f) determining, based on the MER, the WDR and the fixed amount of the pre-made wet composition, an adjusted amount of each of the at least two pre-made dry compositions to obtain the dry portion of the nutritionally complete mixed diet;

g) combining the wet portion and the dry portion to obtain a nutritionally complete mixed diet;

wherein none of the selected distinct pre-made dry compositions consists of a nutritionally complete diet on its own.

In certain embodiments, in addition to the individual general animal profile created based on user input, the user can also input information obtained from a biological sample of the animal.

The analysis provides information that enhances the animal profile information and can be used to modify and refine the animal food composition by suggesting a different pre-manufactured dry or wet composition, adding specific additive ingredients, removing specific additive ingredients, and/or changing the amount of any included additive ingredient from the pet product formulation to enable the new formulation to better meet the needs of the pet. In certain embodiments, the additional nutritional and biological analyses information can be conveyed to the animal's veterinarian to recommend potential therapeutic components to the diet or a therapeutic treatment if appropriate. In an alternative embodiment, the veterinarian can convey the nutritional and biological analyses information to an animal food manufacturer.

The method for providing an individualized nutritionally complete mixed diet for an animal, according to the present disclosure, can thus also include an additional in vitro or ex vivo step of providing a biological sample from the animal, and determining an attribute of a physiological or pathological condition on said sample, thereby providing (or enriching a pre-existing) individual general profile of said animal.

Hence, the disclosure further relates to a method for providing an individualized nutritionally complete mixed diet for an animal, in particular an animal with one or more pathological condition(s), the method including the steps of:

a) providing a biological sample from the animal, and determining an attribute of a physiological or pathological condition on said sample;

b) providing an individual physiological profile of the animal, and optionally an individual pathological profile of the animal, from one or more values indicative of a physiological status, and optionally of a medical status, of the animal, including at least one attribute determined whereby an individual general profile is generated;

c) processing the individual general profile, to determine a nutrient requirement (NR), a maintenance energy requirement (MER), and a wet-dry ratio (WDR) specific to the animal;

d) selecting, based on the NR, one pre-made wet composition from a plurality of distinct pre-made wet compositions, and at least two distinct pre-made dry compositions from a plurality of distinct pre-made dry compositions;

e) determining, based on the MER and the WDR, a fixed amount of the pre-made wet composition to obtain the wet portion of the nutritionally complete mixed diet;

f) determining, based on the MER, the WDR and the fixed amount of the pre-made wet composition, an adjusted amount of each of the at least two distinct pre-made dry compositions to obtain the dry portion of the nutritionally complete mixed diet, g) combining the wet portion and the dry portion to obtain a nutritionally complete mixed diet, wherein none of the selected distinct pre-made dry compositions consists of a nutritionally complete diet on their own, where said nutritionally complete diet is defined as having at least one source of proteins, at least one source of vitamins, at least one source of fats and at least one source of minerals.

2.3. Wet and Dry Compositions

The method of the present disclosure provides an individualized nutritionally complete mixed diet, which includes a pre-made wet composition and at least two distinct pre-made dry compositions. According to the present disclosure, each of the pre-made wet compositions and pre-made dry compositions have a known constitution. In certain embodiments, the method of the present disclosure can include two major steps. The first major step can include determining the nature of the pre-made wet composition and the at least two distinct pre-made dry compositions. In certain embodiments, the first major step can be principally guided by the NR previously determined and specific to the animal to be fed. The second major step can include determining the amount of the pre-made wet composition and the at least two distinct pre-made dry compositions. This second major step can be principally guided by the MER and the WDR which can be determined by methods disclosed herein.

The wet-dry ratio according to the disclosure can be between about 15:85 and about 40:60. According to several embodiments, said wet-dry ratio can be selected from about 15:85, about 16:84, about 17:83, about 18:82, about 19:81, about 20:80, about 21:79, about 22:78, about 23:77, about 24:76, about 25:75, about 26:74, about 27:73, about 28:72, about 29:71, about 30:70, about 31:69, about 32:68, about 33:67, about 34:66, about 35:65, about 36:64, about 37:63, about 38:62, about 39:61 and about 40:60.

The wet-dry ratio can be different according to the breed, the age, the weight, the activity, the lifestyle, the sex, or any other parameter that can be considered to determine the necessary quantity of food to be ingested by the animal.

In certain embodiments, the wet portion can include a pre-made wet composition having a moisture level greater than about 40%, greater than about 50% or greater that about 60% based on weight of the pre-made wet composition.

In certain embodiments, the fixed amount of the pre-made wet composition can be determined, by additionally taking into consideration the limited possibilities to design container suitable to store wet food in good preservation conditions. As an example, but not by the way of limitation, for a cat, the fixed amount of the pre-made wet composition will have to take into consideration not only the MER and the WDR but also the fact that wet food for cat is generally contained in pouch including between about 70 g to about 100 g, such as for example 85 g, of food. It can be decided, as a non-limitative example, to define the fixed amount of the pre-made wet composition such as it corresponds to a pouch (85 g) or half a pouch (42.5 g). Based on this, it will be possible, taking into consideration the MER and the WDR, to determine the necessary amounts of each of the at least two distinct pre-made dry compositions to fulfill completely the energy needs of the cat. In this particular embodiment, the adjustment can be done by the amount of the pre-made dry compositions.

As non-limitative example, for a cat, a fixed amount of a pre-made wet composition can be half a pouch (42.5 g).

In a particular embodiment, the individualized nutritionally complete mixed diet can include at least one source of proteins, at least one source of vitamins, at least one source of fats, and at least one source of minerals.

According to a particular embodiment of the methods disclosed herein, the step of selecting at least two distinct pre-made dry compositions from a plurality of distinct pre-made dry compositions can include selecting at least 3, 4, 5 or even more than 5 distinct pre-made dry compositions from a plurality of distinct pre-made dry compositions.

According to a particular embodiment of the methods disclosed herein, said at least two distinct pre-made dry compositions can be selected from a set of 5 or more distinct pre-made dry compositions. According to a particular embodiment of the methods disclosed herein, said at least two distinct pre-made dry compositions can be selected from at least 6, 7, 8, 9 or more distinct pre-made dry compositions.

According to certain particular embodiments of the present disclosure, the at least 5 or more distinct pre-made dry compositions can be selected from a plurality of distinct pre-made dry compositions.

According to certain particular embodiments of the present disclosure, none of the set of distinct pre-made dry compositions addresses individually a specific pathological condition.

According to certain particular embodiments, the animal can be a companion animal such as a pet. In certain particular embodiments, the animal is a feline or a canine animal such as a cat or a dog.

In certain embodiments of the present disclosure, the nutritionally complete mixed diet can contain a wet portion combined with a dry portion, said dry portion containing at least two distinct pre-made dry compositions selected from:

(i) dry composition A with at least about 1.5% of sodium, at least about 38% of protein and no more than about 10% of fat, relative to the total weight of the composition on a dry-matter basis;

(ii) dry composition B with at least about 0.5% of psyllium tegument, at least about 35% of protein, at least about 0.5% of calcium and no more than about 0.7% of phosphorus, relative to the total weight of the composition on a dry-matter basis;

(iii) dry composition C with at least about 37% of protein, at least about 1.5% of sodium, at least about 2.5% of chloride and at least about 0.6% of EPA and/or DHA, relative to the total weight of the composition on a dry-matter basis;

(iv) dry composition D with at least about 20% of TDF, at least about 38% of protein, no more than about 9% of fat and at least about 1.3% of potassium, relative to the total weight of the composition on a dry-matter basis;

(v) dry composition E with at least about 3.5% of linoleic acid, at least about 0.4% of phosphorus and no more than about 7% of TDF, relative to the total weight of the composition on a dry-matter basis;

(vi) dry composition F with at least about 0.55% of EPA and/or DHA, relative to the total weight of the composition on a dry-matter basis;

(vii) dry composition G with at least about 0.8% of EPA and/or DHA and at least about 1.5% of sodium, relative to the total weight of the composition on a dry-matter basis;

(viii) dry composition H with at least about 20% of fat, no more than about 0.5% of calcium and at least about 5% of linoleic acid, relative to the total weight of the composition on a dry-matter basis; and (ix) dry composition I with at least about 4% of psyllium tegument, relative to the total weight of the composition on a dry-matter basis;

(x) dry composition J with no more than about 6 ppm of total copper, relative to the total weight of the composition on a dry-matter basis;

wherein none of the pre-made distinct dry compositions consists of a nutritionally complete diet on their own.

According to certain embodiments, the present disclosure relates to a method for providing an individualized nutritionally complete mixed diet for a cat, in particular a cat with one or more pathological condition(s), said diet including a wet portion containing one pre-made wet composition combined with a dry portion containing at least two distinct pre-made dry compositions, the method including the steps of:

a) providing an individual physiological profile of a cat, and optionally an individual pathological profile of the cat, from one or more values indicative of a physiological status, and optionally a medical status, of the said cat, whereby an individual general profile is generated;

b) processing the individual general profile, to determine a nutrient requirement (NR), a maintenance energy requirement (MER), and a wet-dry ratio (WDR) specific to the cat;

c) selecting, based on the NR, one pre-made wet composition from a plurality of pre-made wet compositions, and at least two distinct pre-made dry compositions from a plurality of distinct pre-made dry compositions;

d) determining, based on the MER and the WDR, a fixed amount of the pre-made wet composition to obtain the wet portion of the nutritionally complete mixed diet;

e) determining, based on the MER, the WDR and the fixed amount of the pre-made wet composition, an adjusted amount of each of the at least two distinct pre-made dry compositions to obtain the dry portion of the nutritionally complete mixed diet;

f) combining the wet portion and the dry portion to obtain a nutritionally complete mixed diet;

wherein none of the selected distinct pre-made dry compositions consists of a nutritionally complete diet on their own;

and wherein said at least two pre-made dry compositions are selected from:

(i) dry composition A with at least about 1.5% of sodium, at least about 38% of protein and no more than about 10% of fat, relative to the total weight of the composition on a dry-matter basis;

(ii) dry composition B with at least about 0.5% of psyllium tegument, at least about 35% of protein, at least about 0.5% of calcium and no more than about 0.7% of phosphorus, relative to the total weight of the composition on a dry-matter basis;

(iii) dry composition C with at least about 37% of protein, at least about 1.5% of sodium, at least about 2.5% of chloride and at least about 0.6% of EPA and/or DHA, relative to the total weight of the composition on a dry-matter basis;

(iv) dry composition D with at least about 20% of TDF, at least about 38% of protein, no more than about 9% of fat and at least about 1.3% of potassium, relative to the total weight of the composition on a dry-matter basis;

(v) dry composition E with at least about 3.5% of linoleic acid, at least about 0.4% of phosphorus and no more than about 7% of TDF, relative to the total weight of the composition on a dry-matter basis;

(vi) dry composition F with at least about 0.55% of EPA and/or DHA, relative to the total weight of the composition on a dry-matter basis;

(vii) dry composition G with at least about 0.8% of EPA and/or DHA and at least about 1.5% of sodium, relative to the total weight of the composition on a dry-matter basis;

(viii) dry composition H with at least about 20% of fat, no more than about 0.5% of calcium and at least about 5% of linoleic acid, relative to the total weight of the composition on a dry-matter basis; and (ix) dry composition I with at least about 4% of psyllium tegument, relative to the total weight of the composition on a dry-matter basis;

(x) dry composition J with no more than about 6 ppm of total copper, relative to the total weight of the composition on a dry-matter basis.

According to certain embodiments of the present disclosure, the nutritionally complete mixed diet contains a wet portion combined with a dry portion, said dry portion containing at least two pre-made dry compositions selected from:

(i) dry composition A' with at least about 1.7% of sodium and no more than about 10% of fat, relative to the total weight of the composition on a dry-matter basis;

(ii) dry composition B' with at least about 40% of protein and at least about 1.5% of calcium, relative to the total weight of the composition on a dry-matter basis;

(iii) dry composition C' with no more than about 6% of fat and no more than about 0.45% of calcium & phosphorus, relative to the total weight of the composition on a dry-matter basis;

(iv) dry composition D' with at least about 22% of fat, at least about 0.55% of EPA and/or DHA and at least about 5% of linoleic acid, relative to the total weight of the composition on a dry-matter basis;

(v) dry composition E' with no more than about 7% of fat, at least about 25% of TDF and at least about 35% of protein, relative to the total weight of the composition on a dry-matter basis;

(vi) dry composition F' with no more than about 12% of protein, at least about 22% of fat, at least about 0.25% of phosphorus, no more than about 0.5% of calcium and at least about 0.7% of EPA and/or DHA, relative to the total weight of the composition on a dry-matter basis;

(vii) dry composition G' with no more than about 0.35% of calcium, no more than about 0.35% of phosphorus, at least about 1.6% of Sodium and at least about 25% of TDF, relative to the total weight of the composition on a dry-matter basis;

(viii) dry composition H' with no more than about 6% of fat and at least about 1.6% of sodium, relative to the total weight of the composition on a dry-matter basis;

(ix) dry composition I' with no more than about 0.21% of sodium and at least about 1.65% of total arginine, relative to the total weight of the composition on a dry-matter basis;

(x) dry composition J' with no more than 6 ppm of total copper and no more than about 20% of fat, relative to the total weight of the composition on a dry-matter basis;

(xi) dry composition K' with at least about 40% of protein and no more than two about 3% of starch, relative to the total weight of the composition on a dry-matter basis; and (xii) dry composition L' with at least about 21% of total dietary fiber, relative to the total weight of the composition on a dry-matter basis;

wherein none of the pre-made distinct dry compositions consists of a nutritionally complete diet on their own.

According to certain embodiments, the present disclosure relates to a method for providing an individualized nutritionally complete mixed diet for a dog, in particular a dog with one or more pathological condition(s), said diet including a wet portion containing one pre-made wet composition combined with a dry portion containing at least two pre-made dry compositions, the method including the steps of:

a) providing an individual physiological profile of a dog, and optionally an individual pathological profile of the dog, from one or more values indicative of a physiological status, and optionally a medical status, of the said dog, whereby an individual general profile is generated;

b) processing the individual general profile, to determine a nutrient requirement (NR), a maintenance energy requirement (MER), and a wet-dry ratio (WDR) specific to the dog;

c) selecting, based on the NR, one pre-made wet composition from a plurality of pre-made wet compositions, and at least two distinct pre-made dry compositions from a plurality of distinct pre-made dry compositions;

d) determining, based on the MER and the WDR, a fixed amount of the pre-made wet composition to obtain the wet portion of the nutritionally complete mixed diet;

e) determining, based on the MER, the WDR and the fixed amount of the pre-made wet composition, an adjusted amount of each of the at least two distinct pre-made dry compositions to obtain the dry portion of the nutritionally complete mixed diet;

f) combining the wet portion and the dry portion to obtain a nutritionally complete mixed diet, wherein none of the selected distinct pre-made dry compositions consists of a nutritionally complete diet on their own;

and wherein said at least two distinct pre-made dry compositions are selected from:

(i) dry composition A' with at least about 1.7% of sodium and no more than about 10% of fat, relative to the total weight of the composition on a dry-matter basis;

(ii) dry composition B' with at least about 40% of protein and at least about 1.5% of calcium, relative to the total weight of the composition on a dry-matter basis;

(iii) dry composition C' with no more than about 6% of fat and no more than about 0.45% of calcium & phosphorus, relative to the total weight of the composition on a dry-matter basis;

(iv) dry composition D' with at least about 22% of fat, at least about 0.55% of EPA and/or DHA and at least about 5% of linoleic acid, relative to the total weight of the composition on a dry-matter basis;

(v) dry composition E' with no more than about 7% of fat, at least about 25% of TDF and at least about 35% of protein, relative to the total weight of the composition on a dry-matter basis;

(vi) dry composition F' with no more than about 12% of protein, at least about 22% of fat, at least about 0.25% of phosphorus, no more than about 0.5% of calcium and at least about 0.7% of EPA and/or DHA, relative to the total weight of the composition on a dry-matter basis;

(vii) dry composition G' with no more than about 0.35% of calcium, no more than about 0.35% of phosphorus, at least about 1.6% of sodium and at least about 25% of TDF, relative to the total weight of the composition on a dry-matter basis;

(viii) dry composition H' with no more than about 6% of fat and at least about 1.6% of sodium, relative to the total weight of the composition on a dry-matter basis;

(ix) dry composition I' with no more than about 0.21% of sodium and at least about 1.65% of total arginine, relative to the total weight of the composition on a dry-matter basis;

(x) dry composition J' with no more than about 6 ppm of total copper and no more than about 20% of fat, relative to the total weight of the composition on a dry-matter basis;

(xi) dry composition K' with at least about 40% of protein and no more than about 23% of starch, relative to the total weight of the composition on a dry-matter basis; and (xii) dry composition L' with at least about 21% of total dietary fiber, relative to the total weight of the composition on a dry-matter basis.

According to certain embodiments of the present disclosure, the nutritionally complete mixed diet can contain a wet portion combined with a dry portion, said wet portion being selected from:

wet composition 1 with no more than about 45 g/Mcal crude fat, no more than about 1.5 g/Mcal phosphorus, at least about 1.6 g/Mcal EPA+DHA, and at least about 240 mg/Mcal glucosamine+chondroitin;

wet composition 2 with at least about 1.8 g/Mcal EPA+DHA, at least about 240 mg/Mcal glucosamine+chondroitin, at least about 40 mg/Mcal zinc, at least about 37.5 mg/Mcal vitamin B5, and at least about 125 mg/Mcal vitamin B3 (niacin);

wet composition 3 with at least about 3 g/Mcal sodium, at least about 50 mg/Mcal L-carnitine, at least about 110 g/Mcal protein, no more than about 35 g/Mcal crude fat, at least about 0.26 g/Mcal Lactium® (milk protein hydrolysate), at least about 0.98 g/Mcal tryptophan, and at least about 200% of the minimum NRC recommended amount in mg/Mcal in essential amino acids;

wet composition 4 with at least about 50 mg/Mcal L-carnitine, at least about 110 g/Mcal protein, no more than about 35 g/Mcal crude fat, at least about 50 mg/Mcal zinc, and at least about 200% of the minimum NRC recommended amount in mg/Mcal in essential amino acids;

wet composition 5 with at least about 1.8 g/Mcal of EPA+DHA, at least about 80% of moisture in the finish product, at least about 0.26 g/Mcal Lactium® (milk protein hydrolysate), at least about 0.98 g/MCal tryptophan, and no more than about 1.7 g/Mcal phosphorus;

wet composition 6 with at least about 9.3 g/Mcal linoleic acid (LA), at least about alpha-linoleic acid (ALA), at least about 37.5 mg/Mcal vitamin B5, and at least about 125 mg/Mcal vitamin B3 (niacin);

wet composition 7 with no more than about 67 g/Mcal protein, no more than about 1 g/Mcal phosphorus, at least about 1.7 g/Mcal potassium, at least about 1 g/Mcal EPA+DHA, at least about 9.3 g/Mcal linoleic acid (LA), and at least about 0.42 g/Mcal alpha-linoleic acid (ALA);

wet composition 8 with at least about 1.5 g/Mcal EPA+DHA, at least about 200 mg/Mcal glucosamine+chondroitin, no more than about 1.5 g/Mcal phosphorus, at least about 9.3 g/Mcal linoleic acid (LA), and at least about 0.42 g/Mcal alpha-linoleic acid (ALA);

wet composition 9 with at least about 1 g/Mcal EPA+DHA, no more than about 1.7 g/Mcal phosphorus at least about 7.6 g/Mcal linoleic acid (LA), and at least about alpha-linoleic acid (ALA);

wet composition 10 with no more than about 35 g/Mcal crude fat, at least about 6 g/Mcal linoleic acid (LA), at least about 1 g/Mcal EPA+DHA, and no more than about 1.7 g/Mcal phosphorus.

According to certain embodiments, the present disclosure relates to a method for providing an individualized nutritionally complete mixed diet for a cat, in particular a cat with one or more pathological condition(s), said diet including a wet portion containing one pre-made wet composition combined with a dry portion containing at least two distinct pre-made dry compositions, the method including the steps of:

a) providing an individual physiological profile of a cat, and optionally an individual pathological profile of the cat, from one or more values indicative of a physiological status, and optionally a medical status, of the said cat, whereby an individual general profile is generated;

b) processing the individual general profile, to determine a nutrient requirement (NR), a maintenance energy requirement (MER), and a wet-dry ratio (WDR) specific to the cat;

c) selecting, based on the NR, one pre-made wet composition from a plurality of pre-made wet compositions, and at least two distinct pre-made dry compositions from a plurality of distinct pre-made dry compositions;

d) determining, based on the MER and the WDR, a fixed amount of the pre-made wet composition to obtain the wet portion of the nutritionally complete mixed diet;

e) determining, based on the MER, the WDR, and the fixed amount of the pre-made wet composition, an adjusted amount of pre-made dry compositions to obtain the dry portion of the nutritionally complete mixed diet, f) combining the wet portion and the dry portion to obtain a nutritionally complete mixed diet;

wherein none of the selected distinct pre-made dry compositions consists of a nutritionally complete diet on their own;

and wherein said one pre-made wet composition can be selected from:

wet composition 1 with no more than about 45 g/Mcal crude fat, no more than about 1.5 g/Mcal phosphorus, at least about 1.6 g/Mcal EPA+DHA, and at least about 240 mg/Mcal glucosamine+chondroitin;

wet composition 2 with at least about 1.8 g/Mcal EPA+DHA, at least about 240 mg/Mcal glucosamine+chondroitin, at least about 40 mg/Mcal zinc, at least about 37.5 mg/Mcal vitamin B5, and at least about 125 mg/Mcal vitamin B3 (niacin);

wet composition 3 with at least about 3 g/Mcal sodium, at least about 50 mg/Mcal L-carnitine, at least about 110 g/Mcal protein, no more than about 35 g/Mcal crude fat, at least about 0.26 g/Mcal Lactium® (milk protein hydrolysate), at least about 0.98 g/Mcal tryptophan, and at least about 200% of the minimum NRC recommended amount in mg/Mcal in essential amino acids;

wet composition 4 with at least about 50 mg/Mcal L-carnitine, at least about 110 g/Mcal protein, no more than about 35 g/Mcal crude fat, at least about 50 mg/Mcal zinc, and at least about 200% of the minimum NRC recommended amount in mg/Mcal in essential amino acids;

wet composition 5 with at least about 1.8 g/Mcal of EPA+DHA, at least about 80% of moisture in the finish product, at least about 0.26 g/Mcal Lactium® (milk protein hydrolysate), at least about 0.98 g/MCal tryptophan, and no more than about 1.7 g/Mcal phosphorus;

wet composition 6 with at least about 9.3 g/Mcal linoleic acid (LA), at least about alpha-linoleic acid (ALA), at least about 37.5 mg/Mcal vitamin B5, and at least about 125 mg/Mcal vitamin B3 (niacin);

wet composition 7 with no more than about 67 g/Mcal protein, no more than about 1 g/Mcal phosphorus, at least about 1.7 g/Mcal potassium, at least about 1 g/Mcal EPA+DHA, at least about 9.3 g/Mcal linoleic acid (LA), and at least about 0.42 g/Mcal alpha-linoleic acid (ALA);

wet composition 8 with at least about 1.5 g/Mcal EPA+DHA, at least about 200 mg/Mcal glucosamine+chondroitin, no more than about 1.5 g/Mcal phosphorus, at least about 9.3 g/Mcal linoleic acid (LA), and at least about 0.42 g/Mcal alpha-linoleic acid (ALA);

wet composition 9 with at least about 1 g/Mcal EPA+DHA, no more than about 1.7 g/Mcal phosphorus at least about 7.6 g/Mcal linoleic acid (LA), and at least about alpha-linoleic acid (ALA);

wet composition 10 with no more than about 35 g/Mcal crude fat, at least about 6 g/Mcal linoleic acid (LA), at least about 1 g/Mcal EPA+DHA, and no more than about 1.7 g/Mcal phosphorus.

According to certain embodiments, the dry portion can contain at least two distinct pre-made dry compositions selected from:

dry composition A with at least about 1.5% of sodium, at least about 38% of protein and no more than about 10% of fat, relative to the total weight of the composition on a dry-matter basis;

dry composition B with at least about 0.5% of psyllium tegument, at least about 35% of protein, at least about 0.5% of calcium and no more than about 0.7% of phosphorus, relative to the total weight of the composition on a dry-matter basis;

dry composition C with at least about 37% of protein, at least about 1.5% of sodium, at least about 2.5% of chloride and at least about 0.6% of EPA and/or DHA, relative to the total weight of the composition on a dry-matter basis;

dry composition D with at least about 20% of TDF at least about 38% of protein, no more than about 9% of fat and at least about 1.3% of potassium, relative to the total weight of the composition on a dry-matter basis;

dry composition E with at least about 3.5% of linoleic acid, at least about 0.4% of phosphorus and no more than about 7% of TDF, relative to the total weight of the composition on a dry-matter basis;

dry composition F with at least about 0.55% of EPA and/or DHA, relative to the total weight of the composition on a dry-matter basis;

dry composition G with at least about 0.8% of EPA/DHA and at least about 1.5% of sodium, relative to the total weight of the composition on a dry-matter basis;

dry composition H with at least about 20% of fat, no more than about 0.5% of calcium and at least about 5% of linoleic acid, relative to the total weight of the composition on a dry-matter basis;

dry composition I with at least about 4% of psyllium tegument, relative to the total weight of the composition on a dry-matter basis;

dry composition J with no more than about 6 ppm of total copper, relative to the total weight of the composition on a dry-matter basis;

dry composition A' with at least about 1.7% of sodium and no more than about 10% of fat, relative to the total weight of the composition on a dry-matter basis;

dry composition B' with at least about 40% of protein and at least about 1.5% of calcium, relative to the total weight of the composition on a dry-matter basis;

dry composition C' with no more than about 6% of fat and no more than about of calcium & phosphorus, relative to the total weight of the composition on a dry-matter basis;

dry composition D' with at least about 22% of fat, at least about 0.55% of EPA and/or DHA and at least about 5% of linoleic acid, relative to the total weight of the composition on a dry-matter basis;

dry composition E' with no more than about 7% of fat, at least about 25% of TDF and at least about 35% of protein, relative to the total weight of the composition on a dry-matter basis;

dry composition F' with no more than about 12% of protein, at least about 22% of fat, at least about 0.25% of phosphorus, no more than about 0.5% of calcium and at least about 0.7% of EPA and/or DHA, relative to the total weight of the composition on a dry-matter basis;

dry composition G' with no more than about 0.35% of calcium, no more than about 0.35% of phosphorus, at least about 1.6% of sodium and at least about 25% of TDF, relative to the total weight of the composition on a dry-matter basis;

dry composition H' with no more than about 6% of fat and at least about 1.6% of sodium, relative to the total weight of the composition on a dry-matter basis;

dry composition I' with no more than about 0.21% of sodium and at least about 1.65% of total arginine, relative to the total weight of the composition on a dry-matter basis;

dry composition J' with no more than about 6 ppm of total copper and no more than about 20% of fat, relative to the total weight of the composition on a dry-matter basis;

dry composition K' with at least about 40% of protein and no more than about 23% of starch, relative to the total weight of the composition on a dry-matter basis;

dry composition L' with at least about 21% of total dietary fiber, relative to the total weight of the composition on a dry-matter basis;

wherein none of the pre-made distinct dry compositions consists of a nutritionally complete diet on its own; and the wet portion can include one pre-made wet composition selected from:

wet composition 1 with no more than about 45 g/Mcal crude fat, no more than 1.5 g/Mcal phosphorus, at least about 1.6 g/Mcal EPA+DHA, and at least about 240 mg/Mcal glucosamine+chondroitin;

wet composition 2 with at least about 1.8 g/Mcal EPA+DHA, at least about 240 mg/Mcal glucosamine+chondroitin, at least about 40 mg/Mcal zinc, at least about 37.5 mg/Mcal vitamin B5, and at least about 125 mg/Mcal vitamin B3 (niacin);

wet composition 3 with at least about 3 g/Mcal sodium, at least about 50 mg/Mcal L-carnitine, at least about 110 g/Mcal protein, no more than about 35 g/Mcal crude fat, at least about 0.26 g/Mcal Lactium® (milk protein hydrolysate), at least about 0.98 g/Mcal tryptophan, and at least about 200% of the minimum NRC recommended amount in mg/Mcal in essential amino acids;

wet composition 4 with at least about 50 mg/Mcal L-carnitine, at least about 110 g/Mcal protein, no more than about 35 g/Mcal crude fat, at least about 50 mg/Mcal zinc, and at least about 200% of the minimum NRC recommended amount in mg/Mcal in essential amino acids;

wet composition 5 with at least about 1.8 g/Mcal of EPA+DHA, at least about 80% of moisture in the finish product, at least about 0.26 g/Mcal Lactium® (milk protein hydrolysate), at least about 0.98 g/MCal tryptophan, and no more than about 1.7 g/Mcal phosphorus;

wet composition 6 with at least about 9.3 g/Mcal linoleic acid (LA), at least about alpha-linoleic acid (ALA), at least about 37.5 mg/Mcal vitamin B5, and at least about 125 mg/Mcal vitamin B3 (niacin);

wet composition 7 with no more than about 67 g/Mcal protein, no more than about 1 g/Mcal phosphorus, at least about 1.7 g/Mcal potassium, at least about 1 g/Mcal EPA+DHA, at least about 9.3 g/Mcal linoleic acid (LA), and at least about 0.42 g/Mcal alpha-linoleic acid (ALA);

wet composition 8 with at least about 1.5 g/Mcal EPA+DHA, at least about 200 mg/Mcal glucosamine+chondroitin, no more than about 1.5 g/Mcal phosphorus, at least about 9.3 g/Mcal linoleic acid (LA), and at least about 0.42 g/Mcal alpha-linoleic acid (ALA);

wet composition 9 with at least about 1 g/Mcal EPA+DHA, no more than about 1.7 g/Mcal phosphorus at least about 7.6 g/Mcal linoleic acid (LA), and at least about alpha-linoleic acid (ALA);

wet composition 10 with no more than about 35 g/Mcal crude fat, at least about 6 g/Mcal linoleic acid (LA), at least about 1 g/Mcal EPA+DHA, and no more than about 1.7 g/Mcal phosphorus.

According to certain embodiments, the present disclosure relates to a method for providing an individualized nutritionally complete mixed diet for a pet, in particular a pet with one or more pathological condition(s), said diet including a wet portion containing one pre-made wet composition combined with a dry portion containing at least two pre-made dry compositions, the method including the steps of:

a) providing an individual physiological profile of a pet, and optionally an individual pathological profile of the pet, from one or more values indicative of a physiological status, and optionally of a medical status, of the said pet, whereby an individual general profile is generated;

b) processing the individual general profile, to determine a nutrient requirement (NR), a maintenance energy requirement (MER), and a wet-dry ratio (WDR) specific to the pet;

c) selecting, based on the NR, 1 pre-made wet composition from a plurality of pre-made wet compositions, and at least two distinct pre-made dry compositions from a plurality of distinct pre-made dry compositions;

d) determining, based on the MER and the WDR, a fixed amount of the pre-made wet composition to obtain the wet portion of the nutritionally complete mixed diet;

e) determining, based on the MER, the WDR and the fixed amount of the pre-made wet composition, an adjusted amount of each of the at least two pre-made dry compositions to obtain the dry portion of the nutritionally complete mixed diet;

f) combining the wet portion and the dry portion to obtain a nutritionally complete mixed diet;

wherein none of the selected distinct pre-made dry compositions consists of a nutritionally complete diet on their own;

and wherein said at least two distinct pre-made dry compositions are selected from:

(i) dry composition A with at least about 1.5% of sodium, at least about 38% of protein and no more than about 10% of fat, relative to the total weight of the composition on a dry-matter basis;

(ii) dry composition B with at least about 0.5% of psyllium tegument, at least about 35% of protein, at least about 0.5% of calcium and no more than about 0.7% of phosphorus, relative to the total weight of the composition on a dry-matter basis;

(iii) dry composition C with at least about 37% of protein, at least about 1.5% of sodium, at least about 2.5% of chloride and at least about 0.6% of EPA and/or DHA, relative to the total weight of the composition on a dry-matter basis;

(iv) dry composition D with at least about 20% of TDF, at least about 38% of protein, no more than about 9% of fat and at least about 1.3% of potassium, relative to the total weight of the composition on a dry-matter basis;

(v) dry composition E with at least about 3.5% of linoleic acid, at least about 0.4% of phosphorus and no more than about 7% of TDF, relative to the total weight of the composition on a dry-matter basis;

(vi) dry composition F with at least about 0.55% of EPA and/or DHA, relative to the total weight of the composition on a dry-matter basis;

(vii) dry composition G with at least about 0.8% of EPA and/or DHA and at least about 1.5% of sodium, relative to the total weight of the composition on a dry-matter basis;

(viii) dry composition H with at least about 20% of fat, no more than about 0.5% of calcium and at least about 5% of linoleic acid, relative to the total weight of the composition on a dry-matter basis; and (ix) dry composition I with at least about 4% of psyllium tegument, relative to the total weight of the composition on a dry-matter basis;

(x) dry composition J with no more than about 6 ppm of total copper, relative to the total weight of the composition on a dry-matter basis;

(xi) dry composition A' with at least about 1.7% of sodium and no more than about 10% of fat, relative to the total weight of the composition on a dry-matter basis;

(xii) dry composition B' with at least about 40% of protein and at least about 1.5% of calcium, relative to the total weight of the composition on a dry-matter basis;

(xiii) dry composition C' with no more than about 6% of fat and no more than about 0.45% of calcium & phosphorus, relative to the total weight of the composition on a dry-matter basis;

(xiv) dry composition D' with at least about 22% of fat, at least about 0.55% of EPA and/or DHA and at least about 5% of linoleic acid, relative to the total weight of the composition on a dry-matter basis;

(xv) dry composition E' with no more than about 7% of fat, at least about 25% of TDF and at least about 35% of protein, relative to the total weight of the composition on a dry-matter basis;

(xvi) dry composition F' with no more than about 12% of protein, at least about 22% of fat, at least about 0.25% of phosphorus, no more than about 0.5% of calcium and at least about 0.7% of EPA and/or DHA, relative to the total weight of the composition on a dry-matter basis;

(xvii) dry composition G' with no more than about 0.35% of calcium, no more than about 0.35% of phosphorus, at least about 1.6% of sodium and at least about 25% of TDF, relative to the total weight of the composition on a dry-matter basis;

(xviii) dry composition H' with no more than about 6% of fat and at least about 1.6% of sodium, relative to the total weight of the composition on a dry-matter basis;

(xix) dry composition I' with no more than about 0.21% of sodium and at least 1 about 0.65% of total arginine, relative to the total weight of the composition on a dry-matter basis;

(xx) dry composition J' with no more than about 6 ppm of total copper and no more than about 20% of fat, relative to the total weight of the composition on a dry-matter basis;

(xi) dry composition K' with at least about 40% of protein and no more than about 23% of starch, relative to the total weight of the composition on a dry-matter basis;

(xii) dry composition L' with at least about 21% of total dietary fiber, relative to the total weight of the composition on a dry-matter basis;

and wherein said one pre-made wet composition is selected from:

wet composition 1 with no more than about 45 g/Mcal crude fat, no more than about 1.5 g/Mcal phosphorus, at least about 1.6 g/Mcal EPA+DHA, and at least about 240 mg/Mcal glucosamine+chondroitin;

wet composition 2 with at least about 1.8 g/Mcal EPA+DHA, at least about 240 mg/Mcal glucosamine+chondroitin, at least about 40 mg/Mcal zinc, at least about 37.5 mg/Mcal vitamin B5, and at least about 125 mg/Mcal vitamin B3 (niacin);

wet composition 3 with at least about 3 g/Mcal sodium, at least about 50 mg/Mcal L-carnitine, at least about 110 g/Mcal protein, no more than about 35 g/Mcal crude fat, at least about 0.26 g/Mcal Lactium® (milk protein hydrolysate), at least about 0.98 g/Mcal tryptophan, and at least about 200% of the minimum NRC recommended amount in mg/Mcal in essential amino acids;

wet composition 4 with at least 50 mg/Mcal L-carnitine, at least about 110 g/Mcal protein, no more than about 35 g/Mcal crude fat, at least about 50 mg/Mcal zinc, and at least about 200% of the minimum NRC recommended amount in mg/Mcal in essential amino acids;

wet composition 5 with at least about 1.8 g/Mcal of EPA+DHA, at least about 80% of moisture in the finish product, at least about 0.26 g/Mcal Lactium® (milk protein hydrolysate), at least about 0.98 g/MCal tryptophan, and no more than about 1.7 g/Mcal phosphorus;

wet composition 6 with at least about 9.3 g/Mcal linoleic acid (LA), at least about alpha-linoleic acid (ALA), at least about 37.5 mg/Mcal vitamin B5, and at least about 125 mg/Mcal vitamin B3 (niacin);

wet composition 7 with no more than about 67 g/Mcal protein, no more than about 1 g/Mcal phosphorus, at least about 1.7 g/Mcal potassium, at least about 1 g/Mcal EPA+DHA, at least about 9.3 g/Mcal linoleic acid (LA), and at least about 0.42 g/Mcal alpha-linoleic acid (ALA);

wet composition 8 with at least about 1.5 g/Meal EPA+DHA, at least about 200 mg/Mcal glucosamine+chondroitin, no more than about 1.5 g/Mcal phosphorus, at least about 9.3 g/Mcal linoleic acid (LA), and at least about 0.42 g/Mcal alpha-linoleic acid (ALA);

wet composition 9 with at least about 1 g/Mcal EPA+DHA, no more than about 1.7 g/Mcal phosphorus at least about 7.6 g/Mcal linoleic acid (LA), and at least about 0.42 g/Mcal alpha-linoleic acid (ALA);

wet composition 10 with no more than about 35 g/Mcal crude fat, at least about 6 g/Mcal linoleic acid (LA), at least about 1 g/Mcal EPA+DHA, and no more than about 1.7 g/Mcal phosphorus.

In certain embodiments, the step of selecting at least two distinct pre-made dry compositions from the plurality of distinct pre-made dry compositions can include or consist of selecting at least 3, 4, 5 or 6 distinct pre-made dry compositions.

The selected distinct pre-made dry compositions can then be mixed, and optionally further processed (which can thus include being heated, cooled down, grinded and/or lyophilized), in order to provide the dry portion of the individualized nutritionally complete mixed diet.

In certain embodiments, the pre-made dry compositions can be presented as a powder or crumbs, including a white powder or solid form. A powder is useful to be added on the main food of the animal. Other forms can include solid pellets, granules, tablets or any other equivalent.

In certain embodiments, the pre-made wet composition can be presented in chunk form, more particularly chunks in gravy. In certain particular embodiments, the pre-made wet composition can include or consist of chunks and gravy, chunks in jelly, loaf, mousse, terrine, bites form or any other equivalent.

2.4. Implementation

It will be readily understood herein that the provision of an individualized nutritionally complete mixed diet from pre-made wet and dry compositions can be achieved through the same device as the one responsible for the other steps of the method described herein. Yet, in certain embodiments, provision of an individualized nutritionally complete mixed diet from pre-made wet and dry compositions can be achieved through another device, or even remotely.

According to some embodiments, the step of providing the individualized nutritionally complete mixed diet can include the step of the selected one pre-made wet composition and at least two distinct pre-made dry compositions to be transported to specific locations, such as retail locations.

In certain embodiments, the step of providing the individualized nutritionally complete mixed diet can immediately follow the step of selecting the one pre-made wet composition and the at least two distinct pre-made dry composition; or alternatively it can occur at a different time. For instance, such pre-made wet composition and such at least two pre-made dry compositions can be stored over a certain time, and the step of providing the individualized nutritionally complete mixed diet from those pre-made wet composition and pre-made dry compositions can occur at a later time and at a different place.

According to certain other embodiments, the wet portion, i.e., the fixed amount of the pre-made wet composition, can be prepared and stored over a certain time and the dry portion, i.e., the adjusted amount of each of the at least two pre-made dry compositions, can be prepared, mixed and stored also over a certain time and in the same or a different place.

According to certain other embodiments, the adjusted amount of each of the at least two distinct pre-made dry compositions can also be prepared and stored separately, in order to be mixed together later and/or in a different place so as to provide the dry portion of the nutritionally complete mixed diet.

According to certain other embodiments of the present disclosure, the selection of the pre-made wet composition and of the at least two distinct pre-made dry compositions can be realized simultaneously or sequentially. It means that the method can be designed to have both selections done simultaneously taking into consideration the nutrients level provided by both wet and dry portions to fulfill the NR. It means also that one can be done before the other. For example, in certain embodiments, the wet pre-made composition can be selected first based on the NR and available wet compositions and then the at least two distinct pre-made dry compositions can be selected, taking into consideration the nutrient levels provided by the wet portion, in order to fulfill the NR. In certain other embodiments, the at least two distinct pre-made dry compositions can be selected first and then the pre-made wet composition can be selected. All these ways of implementation of the method according to the disclosure allow to take into consideration other external factors and allow a flexibility to adapt the method.

3. Computer-Implemented Methods, System Architectures, and Devices

In certain embodiments, the present disclosure relates to a device/apparatus for performing the methods for preparing the individualized nutritionally complete mixed food diet described herein. This apparatus can be specially constructed for the required purposes, or it can include a general-purpose computer selectively activated or reconfigured by a computer program stored in the computer. The method described herein can thus include, or rely partly on, a computer-implemented method.

Hence, according to another aspect, the disclosure also relates to a device for providing an individualized nutritionally complete mixed diet for an animal, having means adapted to execute the steps of the method described above.

Hence, according to another aspect, the disclosure relates to a computer program including instructions to cause this device to execute the steps of the method described herein.

Hence, according to another aspect, the disclosure relates to a computer-readable medium having stored thereon the computer program described above. Thus, in one embodiment, the disclosure provides a non-transitory computer-readable medium storing sequences of programmed instructions formatted to cause execution of one or more of the methods described herein when executed by one or more processors.

In certain embodiments, the computer program can be stored in a computer readable storage medium, such as, but is not limited to, read-only memories (ROMs), random access memories (RAMs), EPROMs, EEPROMs, flash memory, magnetic or optical cards, any type of disk including floppy disks, optical disks, CD-ROMs, and magnetic-optical disks, or any type of media suitable for storing electronic instructions, and each coupled to a computer system interconnect.

As will be appreciated by one of ordinary skill in the art, the systems and methods disclosed herein can be embodied as a method, a data processing system, a device for data processing, and/or a computer program product. Accordingly, the disclosed systems and methods can take the form of an entirely software embodiment, an entirely hardware embodiment, and/or an embodiment combining aspects of both software and hardware. Furthermore, the disclosed systems and methods can take the form of a computer program product on a computer-readable storage medium having computer-readable program code means embodied in the storage medium. Any suitable computer-readable storage medium can be utilized, including hard disks, CD-ROM, optical storage devices, magnetic storage devices, and/or the like.

The algorithms and displays presented herein are not inherently related to any particular computer or other apparatus. Various general-purpose systems can be used with programs in accordance with the teachings herein, or it can prove convenient to construct a more specialized apparatus to perform the required method operations. The structure for a variety of these systems will appear in the description above. In addition, the present examples are not described with reference to any particular programming language, and various examples can thus be implemented using a variety of programming languages.

As described in greater detail herein, embodiments of the disclosure provide a software application through which a user can receive customized information relating to an animal's health and/or optimal growth as displayed on a graphical user interface based on data input relating to a specific animal. Furthermore, the user can customize, via a selection of at least one biomarker, the information received, such as animal growth or health information, displayed on a graphical user interface from which the software application can apply and display relevant health information and/or an intervention recommendation.

The present disclosure can thus be present in the form of a device (i.e., a computer system and/or a software application platform) which can provide a user with the ability to receive customized information relating to an animal's health and/or optimal growth as displayed on a graphical user interface based on data input relating to a specific animal. In one embodiment, the computer system is a distributed computer system programmed to utilize Client-Server architecture. Specifically, a user can input data into an embodiment, for example, an animal specific biomarker, and subsequently receive identification relating to a specific subgroup of individual animal(s).

In some embodiments, a device (i.e., a computer system and/or a software application platform) for providing an individualized nutritionally complete mixed diet for an animal is disclosed. The device can include a processor and memory storing instructions that, when executed by the processor, cause the device (i.e., the computer system and/or the software application platform) to carry out the method described supra.

For example, the device (i.e., the computer system) can employ various integrated circuit components (e.g., memory elements, processing elements, logic elements, look-up tables, and the like), which can carry out a variety of functions under the control of one and/or more microprocessors and/or other control devices. Similarly, the software elements can be implemented with any programming and/or scripting language such as C, C++, Java, COBOL, assembler, PERL, Visual Basic, SQL Stored Procedures, extensible markup language (XML), hypertext markup language (HTML), SDML, DHTML, HDML, VRML, with the various algorithms being implemented with any combination of data structures, objects, processes, routines and/or other programming elements. Further, the device could employ any number of conventional techniques for data transmission, signaling, data processing, network control, and the like.

In yet other embodiments, a non-transitory computer-readable medium, storing instructions that, when executed by a processor, cause a device (i.e., a computer system) to provide an individualized nutritionally complete diet for an animal is disclosed.

The device (i.e., the computer system) can perform the method operations described supra.

The device/system can further include a user interface, especially an electronic user interface, configured to obtain a user input, including one or more values indicative of a general status of the said animal. Hence, according to some embodiments, the electronic user interface can be configured to obtain a user input including one or more values selected from: an animal's name, species, age, weight, gender, breed, spayed/neutered, activity level, breeding status, digestive health, medical history and genetic information, current health status, body condition, feeding method, snack schedule, and flavor preferences.

According to some embodiments, the present disclosure relates to a device for providing an individualized nutritionally complete mixed diet for an animal, having means adapted to execute the steps of:

a) providing an individual physiological profile of an animal from one or more values indicative of a physiological status of the animal, whereby an individual general profile is generated;

b) processing the individual general profile to determine a nutrient requirement (NR), a maintenance energy requirement (MER), and a wet-dry ratio (WDR) specific to the animal;

c) selecting, based on the NR, one pre-made wet composition from a plurality of pre-made wet compositions, and at least two distinct pre-made dry compositions from a plurality of distinct pre-made dry compositions;

d) determining, based on the MER and the WDR, a fixed amount of the pre-made wet composition to obtain the wet portion of the nutritionally complete mix diet;

e) determining, based on the MER, the WDR, and the fixed amount of the pre-made wet composition, an adjusted amount of each of the at least two pre-made dry compositions to obtain the dry portion of the nutritionally complete mixed diet;

f) combining the wet portion and the dry portion to obtain a nutritionally complete mixed diet;

wherein none of the selected distinct pre-made dry compositions includes a nutritionally complete diet on their own.

In some embodiments of the disclosure, the device can have a further mean adapted to execute the step of providing an individual pathological profile of an animal from one or more values indicative of a medical status of the said animal.

According to some embodiments, the present disclosure relates to a device for providing an individualized nutritionally complete mixed diet for an animal with one or more pathological condition(s).

According to some embodiments, the device/system can further include an ordering device configured to contact a server.

In one embodiment, the disclosure provides a distributed computer system including a server computer that is communicatively coupled to one or more client computing devices over a network. Said network can be any combination of one or more data communication networks including local area networks, wide area networks, internetworks, or internets, using any of wireline or wireless links, including terrestrial or satellite links. The network(s) can be implemented by any medium or mechanism that provides for the exchange of data. The various elements of the distributed computer system can also have direct (wired or wireless) communications links. The various elements of the distributed computer system can each include an interface compatible with the network(s) and can be programmed or configured to use standardized protocols for communication across the networks such as TCP/IP, Bluetooth, or higher-layer protocols such as HTTP, TLS, and the like.

In one embodiment, a client computing device can be a computer that includes hardware capable of communicatively coupling the device to one or more server computers over one or more service provides. For example, the client computing device can include a network card that communicates with the server computer through a home or office wireless router that is communicatively coupled to an internet service provider (ISP). The client computing device can be a smartphone, personal computer, tablet computing device, PDA, laptop, or any other computing device capable of transmitting and receiving information and performing the functions described herein. In one embodiment, the server computer receives one or more values indicative of a physiological status of an animal from the client computing device. In one embodiment, the server computer also receives one or more values indicative of a medical status of the animal.

In one embodiment, the client computing device can include device memory, an operating system, and an application program. In one embodiment, the client computing device hosts and executes the application program, which the client computing device can download and install from server computer, an application store, or another repository. The application program is compatible with the server computer and can communicate with the server computer using an app-specific protocol, parameterized HTTP POST and GET requests, and/or other programmatic calls. In some embodiments, the application program includes a conventional internet browser application that is capable of communicating over the network to other functional elements via HTTP and is capable of rendering dynamic or static HTML, XML, or other markup languages, including displaying text, images, accessing video windows and players, and so forth. In some embodiments, a device display, such as a screen, can be coupled to the client computing device.

In one embodiment, the server computer can be implemented using a server-class computer or other computer having one or more processor cores, co-processors, or other computers. The server computer can be a physical server computer and/or virtual server instance stored in a data center, such as through cloud computing. In one embodiment, the server computer can be implemented using two or more processor cores, clusters, or instances of physical machines or virtual machines, configured in a discrete location, or co-located with other elements in a datacenter, shared computing facility, or cloud computing facility.

In one embodiment, the server computer can store sequences of programmed instructions in computer memory. The computer memory can include any memory accessible by the server computer including a relational database, a data lake, cloud data storage, local hard drives, computer main memory, or any other form of electronic memory. In one embodiment, a plurality of pre-made wet compositions and a plurality of pre-made dry compositions are each stored in computer memory of the server computer. In other embodiments, a plurality of pre-made wet compositions and a plurality of pre-made dry compositions are each stored on-device at the client computing device, or elsewhere.

In various embodiments, the server computer can store and execute sequences of programmed instructions of various types to cause execution of various of the methods described herein. In one embodiment, data processing instructions can be executed by the server computer to process or transform data, such as by executing a programmed or computer-implemented method according to the present disclosure, or to cause data stored in the computer memory to be transmitted to the client computing device over the network. In one embodiment, presentation instructions can be executed by the server computer to cause presentation in a display of a computing device communicating with the server computer over the network or to cause the transmission of display instructions to such a computing device, the display instructions formatted to cause such presentation upon execution.

In one embodiment, the server computer executes data processing instructions to programmatically generate and digitally store an individual general profile of the animal by inferring, at least partly based on the one or more received values, an individual physiological profile of the animal. In one embodiment, the server computer executes data processing instructions to programmatically determine, at least partly based on the individual general profile of the animal, a nutrient requirement (NR), a maintenance energy requirement (MER), and a wet-dry ratio (WDR). In one embodiment, the server computer executes data processing instructions to programmatically select, at least partly based on the NR, one of the pre-made wet compositions and at least two of the pre-made dry compositions, the at least two of the pre-made dry compositions being distinct. In one embodiment, the server computer executes data processing instructions to programmatically determine, at least partly based on the MER and the WDR, a fixed amount of the pre-made wet composition to obtain a wet portion of a nutritionally complete mix diet. In one embodiment, the server computer executes data processing instructions to programmatically determine, at least partly based on the MER, the WDR, and the fixed amount of the pre-made wet composition, an adjusted amount of each of the at least two pre-made dry compositions to obtain a dry portion of the nutritionally complete mixed diet. In one embodiment, the server computer executes presentation instructions to cause displaying, in a graphical user interface, a representation of the nutritionally complete mixed diet, the representation indicating the wet portion and the dry portion. In one embodiment, the server computer can also programmatically generate an individual pathological profile of the animal from the one or more values indicative of the medical status of the animal.

In one embodiment, the disclosure provides a standalone application program embodying the functionality of the aforementioned distributed computer system. The standalone application program cannot require interconnection of a client computing device to a server computer. A customer computing device can download and install the standalone application program from a web server, an application store, or another repository. In one embodiment, the standalone application program is stored on and installed from physical media such as a CD, DVD, flash memory drive, external hard drive, or other physical media.

4. Kits

In certain embodiments, the present disclosure further provides a kit for preparing a nutritionally complete mixed diet for an animal, such as a companion animal, said diet including a wet portion containing one pre-made wet composition combined with a dry portion containing at least two distinct pre-made dry compositions, said kit including
at least two pre-made dry composition selected from:
  dry composition A with at least about 1.5% of sodium, at least about 38% of protein and no more than about 10% of fat, relative to the total weight of the composition on a dry-matter basis;
  dry composition B with at least about 0.5% of psyllium tegument, at least about 35% of protein, at least about 0.5% of calcium and no more than about 0.7% of phosphorus, relative to the total weight of the composition on a dry-matter basis;
  dry composition C with at least about 37% of protein, at least about 1.5% of sodium, at least about 2.5% of chloride and at least about 0.6% of EPA and/or DHA, relative to the total weight of the composition on a dry-matter basis;
  dry composition D with at least about 20% of TDF, at least about 38% of protein, no more than about 9% of fat and at least about 1.3% of potassium, relative to the total weight of the composition on a dry-matter basis;
  dry composition E with at least about 3.5% of linoleic acid, at least about 0.4% of phosphorus and no more than about 7% of TDF, relative to the total weight of the composition on a dry-matter basis;
  dry composition F with at least about 0.55% of EPA and/or DHA, relative to the total weight of the composition on a dry-matter basis;
  dry composition G with at least about 0.8% of EPA/DHA and at least about 1.5% of sodium, relative to the total weight of the composition on a dry-matter basis;
  dry composition H with at least about 20% of fat, no more than about 0.5% of calcium and at least about 5% of linoleic acid, relative to the total weight of the composition on a dry-matter basis;
  dry composition I with at least about 4% of psyllium tegument, relative to the total weight of the composition on a dry-matter basis;

dry composition J with no more than about 6 ppm of total copper, relative to the total weight of the composition on a dry-matter basis;
  dry composition A' with at least about 1.7% of sodium and no more than about 10% of fat, relative to the total weight of the composition on a dry-matter basis;
  dry composition B' with at least about 40% of protein and at least about 1.5% of calcium, relative to the total weight of the composition on a dry-matter basis;
  dry composition C' with no more than about 6% of fat no more than about 0.45% of calcium and no more than about 0.45% of phosphorus, relative to the total weight of the composition on a dry-matter basis;
  dry composition D' with at least about 22% of fat, at least about 0.55% of EPA and/or DHA and at least about 5% of linoleic acid, relative to the total weight of the composition on a dry-matter basis;
  dry composition E' with no more than about 7% of fat, at least about 25% of TDF and at least about 35% of protein, relative to the total weight of the composition on a dry-matter basis;
  dry composition F' with no more than about 12% of protein, at least about 22% of fat, at least about 0.25% of phosphorus, no more than about 0.5% of calcium and at least about 0.7% of EPA and/or DHA, relative to the total weight of the composition on a dry-matter basis;
  dry composition G' with no more than about 0.35% of calcium, no more than about 0.35% of phosphorus, at least about 1.6% of sodium and at least about 25% of TDF, relative to the total weight of the composition on a dry-matter basis;
  dry composition H' with no more than about 6% of fat and at least about 1.6% of sodium, relative to the total weight of the composition on a dry-matter basis;
  dry composition I' with no more than about 0.21% of sodium and at least about 1.65% of total arginine, relative to the total weight of the composition on a dry-matter basis;
  dry composition J' with no more than about 6 ppm of total copper and no more than about 20% of fat, relative to the total weight of the composition on a dry-matter basis;
  dry composition K' with at least about 40% of protein and no more than about 23% of starch, relative to the total weight of the composition on a dry-matter basis;
  dry composition L' with at least about 21% of total dietary fiber, relative to the total weight of the composition on a dry-matter basis;
wherein none of the distinct pre-made dry compositions consists of a nutritionally complete diet on their own;
and at least one pre-made wet composition selected from
  wet composition 1 with no more than about 45 g/Mcal crude fat, no more than about 1.5 g/Mcal phosphorus, at least about 1.6 g/Mcal EPA+DHA, and at least about 240 mg/Mcal glucosamine+chondroitin;
  wet composition 2 with at least about 1.8 g/Mcal EPA+DHA, at least about 240 mg/Mcal glucosamine+chondroitin, at least about 40mg/Mcal zinc, at least about 37.5 mg/Mcal vitamin B5, and at least about 125 mg/Mcal vitamin B3 (niacin);
  wet composition 3 with at least about 3 g/Mcal sodium, at least about 50 mg/Mcal L-carnitine, at least about 110 g/Mcal protein, no more than about 35 g/Mcal crude fat, at least about 0.26 g/Mcal Lactium® (milk protein hydrolysate), at least about 0.98 g/Mcal tryptophan, and at least about 200% of the minimum NRC recommended amount in mg/Mcal in essential amino acids;

wet composition 4 with at least about 50 mg/Mcal L-carnitine, at least about 110 g/Mcal protein, no more than about 35 g/Mcal crude fat, at least about 50 mg/Mcal zinc, and at least about 200% of the minimum NRC recommended amount in mg/Mcal in essential amino acids;

wet composition 5 with at least about 1.8 g/Mcal of EPA+DHA, at least about 80% of moisture in the finish product, at least about 0.26 g/Mcal Lactium® (milk protein hydrolysate), at least about 0.98 g/MCal tryptophan, and no more than about 1.7 g/Mcal phosphorus;

wet composition 6 with at least about 9.3 g/Mcal linoleic acid (LA), at least about alpha-linoleic acid (ALA), at least about 37.5 mg/Mcal vitamin B5, and at least about 125 mg/Mcal vitamin B3 (niacin);

wet composition 7 with no more than about 67 g/Mcal protein, no more than about 1 g/Mcal phosphorus, at least about 1.7 g/Mcal potassium, at least about 1 g/Mcal EPA+DHA, at least about 9.3 g/Mcal linoleic acid (LA), and at least about 0.42 g/Mcal alpha-linoleic acid (ALA);

wet composition 8 with at least about 1.5 g/Mcal EPA+DHA, at least about 200 mg/Mcal glucosamine+chondroitin, no more than about 1.5 g/Mcal phosphorus, at least about 9.3 g/Mcal linoleic acid (LA), and at least about 0.42 g/Mcal alpha-linoleic acid (ALA);

wet composition 9 with at least about 1 g/Mcal EPA+DHA, no more than about 1.7 g/Mcal phosphorus at least about 7.6 g/Mcal linoleic acid (LA), and at least about alpha-linoleic acid (ALA);

wet composition 10 with no more than about 35 g/Mcal crude fat, at least about 6 g/Mcal linoleic acid (LA), at least about 1 g/Mcal EPA+DHA, and no more than about 1.7 g/Mcal phosphorus.

In particular, in certain embodiments, the present description provides a kit for preparing a nutritionally complete mixed diet for an animal, such as a feline, and in particular a cat, including at least two or more distinct pre-made dry compositions selected from:

dry composition A with at least about 1.5% of Sodium, at least about 38% of protein and no more than about 10% of fat, relative to the total weight of the composition on a dry-matter basis;

dry composition B with at least about 0.5% of Psyllium Tegument, at least about 35% of protein, at least about 0.5% of calcium and no more than about 0.7% of Phosphorus, relative to the total weight of the composition on a dry-matter basis;

dry composition C with at least about 37% of protein, at least about 1.5% of Sodium, at least about 2.5% of chloride and at least about 0.6% of EPA and/or DHA, relative to the total weight of the composition on a dry-matter basis;

dry composition D with at least about 20% of TDF, at least about 38% of protein, no more than about 9% of fat and at least about 1.3% of Potassium, relative to the total weight of the composition on a dry-matter basis;

composition E with at least about 3.5% of linoleic acid, at least about 0.4% of Phosphorus and no more than about 7% of TDF, relative to the total weight of the composition on a dry-matter basis;

dry composition F with at least about 0.55% of EPA and/or DHA, relative to the total weight of the composition on a dry-matter basis;

dry composition G with at least about 0.8% of EPA/DHA and at least about 1.5% of Sodium, relative to the total weight of the composition on a dry-matter basis;

dry composition H with at least about 20% of fat, no more than about 0.5% of Calcium and at least about 5% of linoleic acid, relative to the total weight of the composition on a dry-matter basis;

dry composition I with at least about 4% of Psyllium Tegument, relative to the total weight of the composition on a dry-matter basis;

dry composition J with no more than about 6 ppm of total copper, relative to the total weight of the composition on a dry-matter basis.

In some embodiments, the kit according to the disclosure can comprise 2, 3, 4, 5, 6, 7, 8, 9 or 10 distinct pre-made dry compositions.

Alternatively, the present disclosure provides a kit for preparing a nutritionally complete mixed diet for an animal, such as a canine, and in particular a dog, said kit including at least two or more distinct pre-made dry compositions selected from:

dry composition A' with at least about 1.7% of sodium and no more than about 10% of fat, relative to the total weight of the composition on a dry-matter basis;

dry composition B' with at least about 40% of protein and at least about 1.5% of calcium, relative to the total weight of the composition on a dry-matter basis;

dry composition C' with no more than about 6% of fat, no more than about 0.45% of calcium and no more than about 0.45% of phosphorus, relative to the total weight of the composition on a dry-matter basis;

dry composition D' with at least about 22% of fat, at least about 0.55% of EPA and/or DHA and at least about 5% of linoleic acid, relative to the total weight of the composition on a dry-matter basis;

dry composition E' with no more than about 7% of fat, at least about 25% of TDF and at least about 35% of protein, relative to the total weight of the composition on a dry-matter basis;

dry composition F' with no more than about 12% of protein, at least about 22% of fat, at least about 0.25% of phosphorus, no more than about 0.5% of calcium and at least about 0.7% of EPA and/or DHA, relative to the total weight of the composition on a dry-matter basis;

dry composition G' with no more than about 0.35% of calcium, no more than about 0.35% of phosphorus, at least about 1.6% of sodium and at least about 25% of TDF, relative to the total weight of the composition on a dry-matter basis;

dry composition H' with no more than about 6% of fat and at least about 1.6% of sodium, relative to the total weight of the composition on a dry-matter basis;

dry composition I' with no more than about 0.21% of sodium and at least about 1.65% of total arginine, relative to the total weight of the composition on a dry-matter basis;

dry composition J' with no more than about 6 ppm of total copper and no more than 20% of fat, relative to the total weight of the composition on a dry-matter basis;

dry composition K' with at least about 40% of protein and no more than about 23% of starch, relative to the total weight of the composition on a dry-matter basis;

dry composition L' with at least about 21% of total dietary fiber, relative to the total weight of the composition on a dry-matter basis;

wherein none of the distinct pre-made dry compositions consists of a nutritionally complete diet on their own.

In some embodiments, the kit according to the disclosure can comprise 2, 3, 4, 5, 6, 7, 8, 9, 10, 11 or 12 distinct pre-made dry compositions.

Alternatively, the present disclosure provides a kit for preparing a nutritionally complete mixed diet for an animal, such as a feline, and in particular a cat, said kit including at least one pre-made wet compositions selected from:

wet composition 1 with no more than about 45 g/Mcal Crude fat, no more than about 1.5 g/Mcal phosphorus, at least about 1.6 g/Mcal EPA+DHA, and at least about 240 mg/Mcal glucosamine+chondroitin;

wet composition 2 with at least about 1.8 g/Mcal EPA+ DHA, at least about 240 mg/Mcal glucosamine+chondroitin, at least about 40 mg/Mcal zinc, at least about 37.5 mg/Mcal vitamin B5, and at least about 125 mg/Mcal vitamin B3 (niacin);

wet composition 3 with at least about 3 g/Mcal Sodium, at least about 50 mg/Mcal L-carnitine, at least about 110 g/Mcal protein, no more than about 35 g/Mcal crude fat, at least about 0.26 g/Mcal Lactium® (milk protein hydrolysate), at least about 0.98 g/Mcal tryptophan, and at least about 200% of the minimum NRC recommended amount in mg/Mcal in essential amino acids;

wet composition 4 with at least about 50 mg/Mcal L-carnitine, at least about 110 g/Mcal protein, no more than about 35 g/Mcal crude fat, at least about 50 mg/Mcal zinc, and at least about 200% of the minimum NRC recommended amount in mg/Mcal in essential amino acids;

wet composition 5 with at least about 1.8 g/Mcal of EPA+DHA, at least about 80% of moisture in the finish product, at least about 0.26 g/Mcal Lactium® (milk protein hydrolysate), at least about 0.98 g/MCal tryptophan, and no more than about 1.7 g/Mcal phosphorus;

wet composition 6 with at least about 9.3 g/Mcal linoleic acid (LA), at least about 0.42 g/Mcal alpha-linoleic acid (ALA), at least about 37.5 mg/Mcal vitamin B5, and at least about 125 mg/Mcal vitamin B3 (niacin);

wet composition 7 with no more than about 67 g/Mcal protein, no more than about 1 g/Mcal phosphorus, at least about 1.7 g/Mcal potassium, at least about 1 g/Mcal EPA+DHA, at least about 9.3 g/Mcal linoleic acid (LA), and at least about 0.42 g/Mcal alpha-linoleic acid (ALA);

wet composition 8 with at least about 1.5 g/Mcal EPA+ DHA, at least about 200 mg/Mcal glucosamine+chondroitin, no more than about 1.5 g/Mcal phosphorus, at least about 9.3 g/Mcal linoleic acid (LA), and at least about 0.42 g/Mcal alpha-linoleic acid (ALA);

wet composition 9 with at least about 1 g/Mcal EPA+ DHA, no more than about 1.7 g/Mcal phosphorus at least about 7.6 g/Mcal linoleic acid (LA), and at least about alpha-linoleic acid (ALA);

wet composition 10 with no more than about 35 g/Mcal crude fat, at least about 6 g/Mcal linoleic acid (LA), at least about 1 g/Mcal EPA+DHA, and no more than about 1.7 g/Mcal phosphorus.

In some embodiments, the kit according to the disclosure can include 2, 3, 4, 5, 6, 7, 8, 9 or 10 distinct pre-made wet compositions.

EXAMPLES

The presently disclosed subject matter will be better understood by reference to the following Example, which is provided as exemplary of the presently disclosed subject matter, and not by way of limitation.

Example 1: Process Applied to a Cat

The present example describes a method of making an individualized mixed diet for a cat with certain pathological conditions. The details of each step are outlined below.

1. Individual Physiological and Pathological Profile

The first step is to obtain the physiological and pathological profile of the individual cat. Table 3 presents the individual physiological profile of a domestic short hair cat. As shown, this profile includes the cat's sex, age, body condition score (BCS), and weight. As mentioned above, a BCS of 5 equates to an ideal body weight.

Further, Table 3 also presents the pathological profile of the individual cat. It is shown here that the cat has osteoarthritis and renal disorder. The nutritional requirement for a cat with such ailments is described below.

TABLE 3

| Individualized profile for a domestic short hair cat | |
| --- | --- |
| Species | Cat |
| Breed | Domestic short hair |
| Sex | Female |
| Age | 9 years |
| BCS (Body Condition Score) | 4 out of 9 |
| Weight | 3.9 kg |
| Pathology | Osteoarthritis & renal disorder |

2. Nutrient Requirement (NR)

The nutrient requirements for the short haired domestic cat from Part 1 is listed below. Nutrient requirements for each ailment are provided below.

For Osteoarthritis:

Specific levels of EPA and DHA, in addition to and without limitation, of a blend of green lip mussel extract, of chondroitin, and of glucosamine.

For Renal Disorder:

High quality proteins with restricted phosphorus level, omega-3 fatty acids (EPA and DHA) and an antioxidant complex.

3. Maintenance Energy Requirement (MER) and Wet-Dry Ratio (WDR)

The maintenance energy requirement (MER) describes the energy needed to support energy equilibrium and accounts for energy lost during metabolism (metabolized energy). Below, the energy needs of the domestic short hair cat from Part 1 is listed as 204 kcal. The wet-dry ratio (WDR) provides the energy the cat needs to acquire from both the wet and dry food to meet the daily energy needs. Here, the cat is expected to receive 54 kcal from the wet food and 150 kcal from the dry food. A selection of the specific compositions that include the wet and dry foods can then be made.

Daily energy needs: 204 kcal (BCS=4, weight=3.9 kg).

54 kcal from the wet 150 kcal from the dry

The selection of specific compositions of the pre-made wet and pre-made dry food are shown in Tables 4 and 5, respectively. There are 10 different wet food compositions that could have been chosen from. The wet food composition for the short haired domestic cat of Part 1 is chosen to be pre-made wet composition 7.

As described above, the wet food composition 7 contains no more than about 67 g/Mcal protein, no more than about 1 g/Mcal phosphorus, at least about 1.7 g/Mcal potassium, at least about 1 g/Mcal EPA+DHA, at least about 9.3 g/Mcal linoleic acid (LA), and at least about 0.42 g/Mcal alpha-linoleic acid (ALA). The recommended daily ration for this cat is ½ a pouch (as shown in Table 4).

TABLE 4

| Pre-made wet compositions | |
| --- | --- |
| Pre-made wet composition | Quantity |
| Wet 1 | — |
| Wet 2 | — |
| Wet 3 | — |
| Wet 4 | — |
| Wet 5 | — |
| Wet 6 | — |
| Wet 7 | −½ pouch |
| Wet 8 | — |
| Wet 9 | — |
| Wet 10 | — |

Table 5 presents 10 options for pre-made dry compositions. The compositions that are chosen in this particular example are dry F at 33.1%, dry G at 6.1%, and dry H at 60.8%. As noted in the description above, the pre-made dry composition can be dry composition F with at least about 0.55% of EPA and/or DHA, relative to the total weight of the composition on a dry-matter basis, dry composition G with at least about 0.8% of EPA/DHA and at least about 1.5% of sodium, relative to the total weight of the composition on a dry-matter basis, and dry composition H with at least about 20% of fat, no more than about 0.5% of calcium and at least about 5% of linoleic acid, relative to the total weight of the composition on a dry-matter basis.

TABLE 5

| Pre-made dry compositions | |
| --- | --- |
| Pre-made dry compositions | Quantity |
| Dry A | — |
| Dry B | — |
| Dry C | — |
| Dry D | — |
| Dry E | — |
| Dry F | 33.1% |
| Dry G | 6.1% |
| Dry H | 60.8% |
| Dry I | — |
| Dry J | — |

As described in Part 4 below, the dry and wet food compositions provide the cat with low phosphorus content and high EPA/DHA levels. The low phosphate levels are necessary due to the restricted phosphate levels recommended for a cat with renal disorder. Further, the dry food also contains glucosamine, chondroitin, and green lip mussel extract levels that cover the total daily need of the cat, especially as a cat with osteoarthritis is recommended to have these elements in its diet.

4. Amount of the Pre-Made Food Compositions

The final amount of the wet and the dry compositions are chosen to meet the following requirements.

The Wet Food Composition Provides:

low phosphorus high EPA/DHA levels

The Dry Food Composition Provides:

low phosphorus high EPA/DHA levels glucosamine+chondroitin+green lip mussel extract levels that cover the total daily need of the cat.

The amount of each of the wet and the dry compositions are chosen as follows:

Recommended daily ration: ½ pouch per day+39 g of kibbles

It should be appreciated that in the above description of exemplary embodiments of the disclosure, various features of the disclosure are sometimes grouped together in a single embodiment, figure, or description thereof for the purpose of streamlining the disclosure and aiding in the understanding of one or more of the various aspects. This method of disclosure, however, is not to be interpreted as reflecting an intention that the disclosure requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this disclosure.

Furthermore, while some embodiments described herein include some but not other features included in other embodiments, combinations of features of different embodiments are meant to be within the scope of the disclosure, and form different embodiments, as would be understood by those skilled in the art. For example, in the following claims, any of the claimed embodiments can be used in any combination.

Thus, while certain embodiments have been described, those skilled in the art will recognize that other and further modifications can be made thereto without departing from the spirit of the disclosure, and it is intended to claim all such changes and modifications as falling within the scope of the disclosure. For example, functionality can be added or deleted from the block diagrams and operations can be interchanged among functional blocks. Steps can be added or deleted to methods described within the scope of the present disclosure The above disclosed subject matter is to be considered illustrative, and not restrictive, and the appended claims are intended to cover all such modifications, enhancements, and other implementations, which fall within the true spirit and scope of the present disclosure. Thus, to the maximum extent allowed by law, the scope of the present disclosure is to be determined by the broadest permissible interpretation of the following claims and their equivalents and shall not be restricted or limited by the foregoing detailed description. While various implementations of the disclosure have been described, it will be apparent to those of ordinary skill in the art that many more implementations are possible within the scope of the disclosure. Accordingly, the disclosure is not to be restricted except in light of the attached claims and their equivalents.

The invention claimed is:

1. A method for providing an individualized nutritionally complete mixed diet for an animal, said diet comprising a wet portion comprising one pre-made wet composition combined with a dry portion comprising at least two distinct pre-made dry compositions, the method comprising the steps of:

a) providing an individual physiological profile of an animal from one or more values indicative of a physiological status of the animal, whereby an individual general profile is generated;

b) processing the individual general profile to determine a nutrient requirement (NR), a maintenance energy requirement (MER) and a wet-dry ratio (WDR) specific to the animal;

c) selecting, based on the NR, one pre-made wet composition from a plurality of distinct pre-made wet compositions, and at least two distinct pre-made dry compositions from a plurality of distinct pre-made dry compositions, wherein the at least two distinct pre-made dry compositions each independently comprise at least one of:

i) sodium in an amount of at least about 1.5%, ii) fat in an amount of no more than about 20%, iii) fat in an amount of at least about 20%, iv) phosphorous in an amount of no more than about 0.7%, v) protein in an amount of at least about 35%, vi) EPA and/or DHA in an amount of at least about 0.55%, vii) fiber in an amount of at least about 20%, viii) psyllium tegument in an amount of at least about 0.45%, ix) copper in an amount of no more than about 6 ppm, x) arginine in an amount of at least about 1.65%, and xi) linoleic acid in an amount of at least about 3.5%, relative to the total weight of the composition on a dry-matter basis;

d) determining, based on the MER and the WDR, a fixed amount of the pre-made wet composition to obtain the wet portion of the nutritionally complete mixed diet;

e) determining, based on the MER, the WDR and the fixed amount of the pre-made wet composition, an adjusted amount of each of the at least two distinct pre-made dry compositions to obtain the dry portion of the nutritionally complete mixed diet;

f) combining the wet portion and the dry portion to obtain a nutritionally complete mixed diet comprising:

i) protein in an amount of at least about 18 g per 100 g of dry matter of the total composition, and ii) fat in amount of at least about 9 g per 100 g of dry matter of the total composition, wherein none of the said selected distinct pre-made dry compositions comprises a nutritionally complete diet alone.

2. The method of claim 1, wherein the selection of the pre-made wet composition and the at least two pre-made dry compositions in step c) are realized simultaneously or sequentially.

3. The method according to claim 1, further comprising a step of providing an individual pathological profile of the animal from one or more values indicative of a medical status of the animal.

4. The method according to claim 3, wherein the animal is a cat and the one or more values indicative of a medical status of the said animal are selected from the group consisting of Post weight loss, Overweight, Obesity, Osteoarthritis, Mobility risk factors, Chronic Kidney Disease (CKD) Stage I, II, III or IV, Proteinuria, Struvite urolith dissolution, Struvite urolith prevention, Calcium Oxalate urolith (CaOx) prevention, Calcium Phosphate urolith (CaP) prevention, Idiopathic cystitis, Poor skin and coat, Atopy, non-food related dermatopathies, Dental Calculus, Acute or chronic diarrhea, Acute or chronic vomiting, Gastritis, Enteritis, Colitis, Maldigestion, Malabsorption, Diabetes mellitus, Pancreatitis, Exocrine pancreatic insufficiency (EPI), and Hyperlipidemia.

5. The method according to claim 3, wherein the animal is a dog and the one or more values indicative of a medical status of the said animal are selected from the group consisting of Post weight loss, Overweight, Obesity, Osteoarthritis, Mobility risk factors, CKD Stage I, II, III or IV, Proteinuria, Struvite urolith dissolution, Struvite urolith prevention, Calcium Oxalate urolith (CaOx) prevention, Calcium Phosphate urolith (CaP) prevention, Idiopathic cystitis, Poor skin and coat, Atopy, non-food related dermatopathies, Dental Calculus, Acute or chronic diarrhea, Acute or chronic vomiting, Gastritis, Enteritis, Colitis, Maldigestion, Malabsorption, Diabetes mellitus, Pancreatitis, Exocrine pancreatic insufficiency (EPI), Hyperlipidemia, and Adverse food reaction.

6. The method of claim 3, wherein the animal has one or more pathological conditions.

7. The method of claim 1, wherein the WDR ratio is between 15:85 to 40:60.

8. The method according to claim 1, wherein the dry portion comprises at least 5 distinct pre-made dry compositions selected from a plurality of distinct pre-made dry compositions.

9. The method according to claim 1, wherein the pre-made dry compositions have a moisture level ranging from about 1% to about 14% w/w.

10. The method according to claim 9, wherein the said pre-made dry compositions comprise dry kibbles.

11. The method according to claim 1, wherein the wet portion comprises a pre-made wet composition having a moisture level greater than about 60% w/w.

12. The method according to claim 1, wherein the one or more values indicative of a physiological status of the said animal are selected from the group consisting of animal's breed, animal's age, animal's actual weight, animal's targeted weight, animal's Body Condition Score (BCS), animal's activity, animal's lifestyle, animal's sexual status, and animal's gestation status.

13. The method according to claim 1, which comprises a computer-implemented method.

14. The method of claim 1, wherein the nutritionally complete diet further comprises at least one additional ingredient selected from the group consisting of a source of proteins, a source of vitamins, a source of fats and a source of minerals.

15. A device for providing an individualized nutritionally complete mixed diet for an animal comprising a wet portion comprising one pre-made wet composition combined with a dry portion comprising at least two distinct pre-made dry compositions, said device having means adapted to execute the steps of:

a) providing an individual physiological profile of an animal from one or more values indicative of a physiological status of the animal, whereby an individual general profile is generated;

b) processing the individual general profile to determine a nutrient requirement (NR), a maintenance energy requirement (MER) and a wet-dry ratio (WDR) specific to the animal;

c) selecting, based on the NR of the step b), one pre-made wet composition from a plurality of distinct pre-made wet compositions, and at least two distinct pre-made dry compositions from a plurality of distinct pre-made dry compositions, wherein the at least two distinct pre-made dry compositions each independently comprise at least one of:

i) sodium in an amount of at least about 1.5%, ii) fat in an amount of no more than about 20%, iii) fat in an amount of at least about 20%, iv) phosphorous in an amount of no more than about 0.7%, v) protein in an amount of at least about 35%, vi) EPA and/or DHA in an amount of at least about 0.55%, vii) fiber in an amount of at least about 20%, viii) psyllium tegument in an amount of at least about 0.45%, ix) copper in an amount of no more than about 6 ppm, x) arginine in an amount of at least about 1.65%, and xi) linoleic acid in an amount of at least about 3.5%, relative to the total weight of the composition on a dry-matter basis;

d) determining, based on the MER and the WDR, a fixed amount of the pre-made wet composition to obtain the wet portion of the nutritionally complete mixed diet;

e) determining, based on the MER and the WDR, the adjusted amount of each of the at least two pre-made dry compositions and mixing them together to obtain the dry portion of the nutritionally complete mixed diet;

f) combining the wet portion and the dry portion to obtain a nutritionally complete mixed diet comprising:

i) protein in an amount of at least about 18 g per 100 g of dry matter of the total composition, and ii) fat in amount of at least about 9 g per 100 g of dry matter of the total composition;

wherein none of the said selected distinct pre-made dry compositions comprises a nutritionally complete diet alone.

16. A device according to claim 15, having a further means adapted to execute the step of providing an individual pathological profile of an animal from one or more values indicative of a medical status of the said animal.

17. A computer-readable non transitory media having stored thereon a computer program comprising instructions, wherein the computer program when executed by one or more processors causes the device of claim 15 to execute the steps of the method.

\* \* \* \* \*